(12) United States Patent  
Kimura

(10) Patent No.: US 7,120,482 B2
(45) Date of Patent: Oct. 10, 2006

(54) OPTICAL MEASURING APPARATUS AND METHOD

(75) Inventor: Masahiro Kimura, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 227 days.

(21) Appl. No.: 10/713,263

(22) Filed: Nov. 17, 2003

(65) Prior Publication Data

US 2004/0106856 A1 Jun. 3, 2004

(30) Foreign Application Priority Data

Nov. 18, 2002 (JP) .............................. 2002-334155
Nov. 25, 2002 (JP) .............................. 2002-340679

(51) Int. Cl.
*A61B 5/00* (2006.01)
(52) U.S. Cl. ...................................... 600/344; 600/310
(58) Field of Classification Search ................ 600/310, 600/344, 322; 356/300
See application file for complete search history.

(56) References Cited

U.S. PATENT DOCUMENTS

| 5,331,969 A | | 7/1994 | Silberstein |
| 5,787,887 A | * | 8/1998 | Klingenbeck-Regn ...... 600/310 |
| 5,995,866 A | * | 11/1999 | Lemelson .................. 600/476 |
| 6,542,763 B1 | | 4/2003 | Yamashita et al. |
| 6,577,884 B1 | * | 6/2003 | Boas .......................... 600/310 |
| 2001/0029325 A1 | | 10/2001 | Parker |
| 2002/0033454 A1 | | 3/2002 | Cheng et al. |
| 2004/0064149 A1 | * | 4/2004 | Doern et al. ................. 606/130 |

FOREIGN PATENT DOCUMENTS

| JP | 11-164826 A | 6/1999 |
| JP | 11-169361 A | 6/1999 |
| JP | 2001-120554 A | 5/2001 |
| JP | 2001-286449 A | 10/2001 |
| WO | WO-00/57793 A1 | 10/2000 |

* cited by examiner

Primary Examiner—Eric F. Winakur
(74) Attorney, Agent, or Firm—Birch, Stewart, Kolasch & Birch, LLP

(57) ABSTRACT

Optical measuring apparatus is constructed to irradiate near infrared light to a desired portion, such as a head, of a person to be measured, receive arriving light from the desired portion and acquire information about a predetermined substance present in the desired portion on the basis of analysis of data related to the received arriving light. Measuring unit of the apparatus is provided on a cover member removably attachable to the person, and includes at least one light irradiation section for irradiating the near infrared light to the desired portion and at least one light reception section for receiving the arriving light from the desired portion. In a state where the cover member is attached to the person, the light irradiation and reception sections are positioned out of contact with the desired portion.

22 Claims, 16 Drawing Sheets

OPTICAL MEASURING APPARATUS AND METHOD

This Nonprovisional application claims priority under 35 U.S.C. § 119(a) on Patent Application No(s). 2002-334155 and 2002-340679 filed in Japan on Nov. 18, 2002 and Nov. 25, 2002, the entire contents of which are hereby incorporated by reference.

FIELD OF THE INVENTION

The present invention relates generally to optical measuring apparatus and methods, and more particularly to an improved optical measuring apparatus and method which use near infrared light to detect, for example, blood distribution in desired portions of objects to be measured, such as a brain of a person.

BACKGROUND OF THE INVENTION

There have been known techniques for optically measuring blood amount variation in and around a surface layer of a brain of a person by irradiating near infrared light to the head of the person. The known blood amount measuring techniques are based on detection of blood distribution performed by detecting a state of existence of hemoglobin utilizing a difference between light absorbing characteristics of oxygenated hemoglobin and deoxygenated hemoglobin. In the near infrared light measurement by the known optical measuring apparatus based on near infrared light irradiation, a measuring probe unit, which includes a plurality of optical fibers secured to a flexible base plate, is attached to the head of a person to be measured. Near infrared light is irradiated via the optical fibers to the head, and then an analysis is made of diffuse reflected light having passed through a surface layer of the brain and its vicinity. The analysis is intended to identify a blood distribution state in the measured portion of the brain surface layer, to thereby identify active areas of the brain changing during the optical measurement.

An example of the apparatus for performing the above-mentioned optical measurement based on near infrared light irradiation is disclosed in Japanese Patent Application Laid-Open Publication No. HEI-11-164826. The disclosed optical measuring apparatus includes a photo detector for converting, into electricity, light having passed into and then got out of a desired portion of an object to be measured (i.e., to-be-measured object or test subject), and a light detection section including a circuit for amplifying the converted electrical signal or a circuit for distinguishing a given frequency component. The disclosed optical measuring apparatus also includes a bias adjustment circuit and amplifier within the light detection section or at a stage following the light detection section. Signal adjusting value of the bias adjustment circuit and gain of the amplifier are set in accordance with intensity of the passed light and noise contained in the passed light.

Another example of the optical measuring apparatus is disclosed in Japanese Patent Application Laid-Open Publication No. HEI-11-169361, which irradiates light to an object to be measured and acquire information indicative of a status within the to-be-measured object. In the disclosed apparatus, light emitted by a light source, whose intensity can be modified at a desired frequency, is irradiated to the object, and a component of the irradiated light having passed into and then got out of the object is detected and converted into an electrical signal. The converted signal is then passed through a frequency filter, amplified and then subjected to phase detection.

The conventionally-known optical measuring apparatus would, however, present the following two problems.

First Problem:

Where the head of a person is to be optically measured or investigated by use of any one of the above-mentioned optical measuring apparatus utilizing near infrared light, a measuring probe unit is attached to and fixed to the head of the to-be-measured person. In this case, it is necessary to push aside the head hair with a rod-shaped implement and then firmly press respective distal ends of a plurality of optical fibers, provided on the measuring probe unit, into close contact with the skin of the head. Pushing aside the hair is necessary to allow near infrared light to be appropriately irradiated through the optical fibers to the surface of the head skin without being hindered by the hair. The conventional measuring probe unit is constructed to permit "24-point measurement", where the near infrared light is irradiated to eight points or spots of the head skin. For that purpose, there are provided eight light irradiation sections and eight light detection sections on a substantial square area of the probe unit opposed to the head skin.

In the case where such a 24-point measuring probe unit is used, even a skilled human operator would ordinarily take about 20 minutes of preliminary arrangements (preparations) for securing the probe unit to the head of the to-be-measured person while meeting the aforementioned requirements. Further, in fixing the measuring probe unit to the person's head, there is a need to press the inner surface of the probe unit into close contact with the head skin. Thus pressing the inner surface of the probe unit into close contact with the head skin, however, imparts considerable pressure to the head, so that the to-be-measured person may feel a pain in the head and have a uncomfortable feeling during the optical measurement. Further, with the conventional optical measuring apparatus where the measuring probe unit is pressed to closely contact the head skin of the to-be-measured person, the probe unit and hence the distal ends of the optical fibers provided thereon tend to be undesirably displaced as the to-be-measured person moves his or her head. Therefore, the spot of the head skin where the irradiated near infrared light enters (i.e., incident position) and the position where scattering reflected light from the head skin is detected (i.e., reflected light detection position) can not be kept constant, which would adversely influence results of the optical measurement.

Second Problem:

Referring to FIG. 18, if the near infrared light 202 is irradiated from the light irradiation section 200 to the head 201, reflection, refractive transmission and scattering of the irradiated near infrared light 202 are repeated between the head skin 203, skull 204 and cerebrum 205. Then, reflected light 206 due to diffusion and scattering (hereinafter, diffuse/scattering reflected light), having got out of the head 201, is detected by a light detection mechanism 207. Because a plurality of arteries exist in the head skin 203 and its vicinity, the reflected light 206 detected by the optical measuring apparatus would be unavoidably influenced by the arteries 208. For example, where blood distribution in the cerebrum is to be measured, and if the pulsation of the arteries 208 influences, a signal produced due to blood flows in the arteries 208 undesirably overlaps a light detection signal (measurement signal) representative of detected reflected light from the head, so that accurate measurement of the blood distribution in the cerebrum 205 tends to be difficult to achieve.

SUMMARY OF THE INVENTION

In view of the foregoing prior art problems, it is a first object of the present invention to provide an optical measuring apparatus and method which allow a measuring unit to be readily fixed reliably to a desired portion of a to-be-measured object with respective distal ends of a plurality of optical fibers appropriately held in sufficient proximity to the surface of the desired portion without being pressed into close contact with the surface of the desired portion, which can prevent undesired displacement, during optical measurement, of an incident position etc. of near infrared light and allow the measuring unit to be handled with ease, which achieve high-accuracy measurement results, and which can effectively lower physical and psychological loads on a to-be-measured person or the like and reduce time and labor on the part of a measuring operator.

It is a second object of the present invention to provide an optical measuring apparatus and method which can accurately measure distribution, in a brain or other desired portion of a person or the like to be measured, of blood or other biological substance such as glucose, etc.

According to one aspect of the present invention, there is provided an optical measuring apparatus for irradiating near infrared light to a desired portion of an object to be measured, receiving arriving light from the desired portion and extracting or acquiring information about a predetermined substance present in the desired portion on the basis of analysis of data related to the received arriving light. The object to be measured is a living body, preferably a living human body. The optical measuring apparatus includes a measuring unit provided on a cover member removably attachable to the object to be measured. The measuring unit includes at least one light irradiation section for irradiating the near infrared light to the desired portion of the object, and at least one light reception section for receiving the arriving light from the desired portion of the object. In a state where the cover member is duly attached to the object to be measured, the light irradiation section and the light reception section are both positioned out of contact with the desired portion of the object.

In the present invention, the measuring unit to be attached to the object to be measured for optical measurement is provided on the cover member readily attachable to the object, and thus the measuring unit can be attached to the desired portion of the object with ease. In the state where the cover member is duly attached to the object to be measured, one or more light irradiation and detection sections of the measuring unit are reliably prevented from pressing against the skin surface of the object by virtue of f their characteristic mounting structures, which can reduce physical and psychological loads on the object to be measured. Because just attaching the cover member can appropriately position the one or more light irradiation and detection sections at locations preferable for the optical measurement, the necessary measuring operations can be signifycantly simplified.

In an embodiment of the present invention, the object to be measured is a human body, the cover member is a helmet for covering the head of the human body, and the light irradiation section and the light reception section have their respective distal ends positioned on the inner side of the helmet. In the embodiment, it is only necessary to place the helmet on the head when blood distribution or the like in the head of a to-be-measured person is to be optically measured. With the helmet placed on the head, the respective distal ends of the light irradiation and reception sections on the inner side of the helmet are automatically positioned in sufficient proximity to, but out of contact with, the surface of the head.

In the present invention, by only placing on the object to be measured the cover member, such as a helmet, provided with the measuring unit, the measuring unit can be readily attached for desired optical measurement. Thus, the present invention can reduce necessary preparations for the optical measurement and overall time and labor necessary for the optical measurement. Further, because the present invention can eliminate the need for a probing distal end of the light irradiation section etc. to be held in close contact with the head or other body portion of the to-be-measured person, it can alleviate loads on the to-be-measured person. Further, because the measuring unit can be fixed via the cover member to the head or other body portion of the to-be-measured person against accidental displacement, the present invention can reliably prevent unnecessary or undesired displacement of the distal ends of optical fibers of the light irradiation and reception sections, thereby achieving accurate measurement results.

Preferably, the optical measuring apparatus of the present invention further comprises a scanning mechanism, and a condenser lens supported at the distal end of the light irradiation section via the scanning mechanism. During optical measurement by the optical scanning apparatus, the condenser lens can be varied, by the scanning mechanism, in an angular position thereof relative to the surface of the desired portion of the object so as to change an irradiation direction of the near infrared light. Preferably, the scanning mechanism includes a piezoelectric element, and the variation in the angular position (e.g., oscillating movement) of the condenser lens is effected by control of a voltage to be applied to the piezoelectric element. When the cover member is attached to, for example, the head, the hair present between the distal end of the light irradiation section and the surface of a desired surface region of the head to be measured may hinder the passage of the irradiated near infrared light to the surface. In such a case, the condenser lens at the distal end of the light irradiation section is varied in its angular position or orientation via the scanning mechanism, to allow the near infrared light, output from the distal end of an optical fiber of the light irradiation section, to be irradiated directly to a desired head surface region without being hindered by the hair.

Preferably, the light irradiation section is supported in its entirely by the scanning mechanism, and, during the optical measurement by the optical scanning apparatus, the light irradiation section is variable, by the scanning mechanism, in the angular position thereof relative to the surface of the desired portion of the object so as to change the irradiation direction of the near infrared light. This arrangement allows the near infrared light, output from the distal end of the optical fiber of the light irradiation section, to be irradiated directly to the desired head surface region without being hindered by the hair.

Preferably, the optical measuring apparatus of the present invention further comprises an adjustment section that moves the light irradiation section in an axial direction thereof with respect to the surface of the desired portion of the object to thereby adjust a distance between the light irradiation section and the surface of the desired portion, and the light irradiation section is supported by the adjustment mechanism. With this arrangement, the distance between the light irradiation section and the surface of the desired portion can be adjusted as appropriate, to adjust the intensity of the near infrared light to be irradiated to the desired portion of the object and thereby adjust the measuring sensitivity of the measuring apparatus.

In the optical measuring apparatus, the above-mentioned arriving light is diffuse/scattering reflected light from the desired portion of the object to be measured.

With the arrangement that the irradiated near infrared light is deflected via the scanning mechanism to scan the desired portion of the object to be measured, the present invention can create a measuring environment capable of eliminating influences of the hair present in the desired portion, thereby attaining accurate measurement. By increasing the scanned scope of the desired portion, the present invention can acquire information about a greater region of the desired portion. Furthermore, because the near infrared light can be irradiated directly to a suitable spot of the desired portion by virtue of the deflection of the light effected by the scanning mechanism, the present invention can reduce the power of the light to be used.

According to another aspect of the present invention, there is provided an optical measuring apparatus for irradiating near infrared light to a desired portion of a living body to be measured, receiving arriving light from the desired portion of the living body and acquiring information about a predetermined biological substance present in the desired portion on the basis of analysis of data related to the received arriving light. The arriving light from the desired portion of the living body is diffuse/scattering reflected light produced by the irradiated near infrared light entering the desired portion of the living portion, then repeating reflection, refractive transmission and scattering in the desired portion and then getting out of the desired portion toward the light detection section. The optical measuring apparatus comprises: a light irradiation mechanism for irradiating the near infrared light to the desired portion of the living body to be measured; a light detection mechanism for detecting the arriving or reflected light from the desired portion of the living body and thereby generating a reflected light detection signal representative of the detected reflected light; a pulse wave detection section for detecting a pulse wave in another portion of the living body separate from the desired portion and thereby generating a pulse wave signal indicative of the detected pulse wave; an arithmetic operation section for subtracting pulse wave data, obtained on the basis of the signal generated by the pulse wave detection section, from measurement data obtained on the basis of the arriving light detected by the light detection mechanism; and a display section for displaying a result of an arithmetic operation performed by the arithmetic operation section. With the arrangement that the pulse wave data is subtracted from the measurement data (i.e., reflected light measurement data), a noise signal component corresponding to pulse waves of arteries in the desired portion can be removed from the reflected light detection signal, which can acquire information of the biological substance with high accuracy.

Preferably, in the optical measuring apparatus of the present invention, the light irradiation mechanism includes at least one light source for emitting light of a wavelength in a near infrared range, and at least one optical fiber for transmitting therethrough the light emitted by the light source. If the light irradiation mechanism includes a plurality of optical fibers, the present invention can simultaneously perform optical measurement at a plurality of spots of the desired portion and can thereby measure distribution of the biological substance in the desired portion; thus, more accurate information of the biological substance can be provided. Further, if the optical measuring apparatus employs a plurality of light sources capable of emitting light of different wavelengths, then the present invention can measure the biological substance using the light of the different wavelengths; thus, analyzing the respective diffuse reflections of the different light can attain more reliable information of the biological substance.

In a preferred embodiment, the light irradiation mechanism includes a light source for emitting light of a wavelength in a near infrared range, a spectroscope for dispersing the light emitted by the light source, and an optical fiber for outputting the light dispersed by the spectroscope. Even where only one light source is employed, the provision of the spectroscope allows the optical measuring apparatus to irradiate near infrared light of a plurality of wavelengths.

Preferably, in the optical measuring apparatus of the present invention, the light detection mechanism includes a photo detector section sensitive to a plurality of different near infrared wavelength regions, so that diffuse reflected light in the near infrared arrange can be detected with high accuracy.

In a preferred embodiment, the other portion (auxiliary measured portion) of the living body is located substantially the same distance from the heart of the living body as the desired portion (principal measured portion), so that there can be obtained pulse wave data that are similar to, and have no substantial phase difference etc. from, those obtained from the principal measured portion of the living body.

Preferably, in the optical measuring apparatus of the invention, the other portion of the living body is an earlobe. Using the earlobe as the other or auxiliary measured portion, it is possible to readily acquire the pulse wave data.

Preferably, in the optical measuring apparatus of the invention, the information about the predetermined biological substance pertains to at least one of a concentration of oxygenated hemoglobin, a concentration of deoxygenated hemoglobin, a concentration of all the hemoglobin and an amount of blood in the desired portion. With such an arrangement, the optical measuring apparatus can measure an amount of blood in the desired portion of the living body, and, because blood distribution in the desired body can be measured, it is possible to observe or monitor a working status of the desired portion. The information about the pre-determined biological substance may concern a concentration of glucose in the desired portion, in which case it is possible to monitor sugar metabolism in the desired portion. The desired portion is, for example, the head of a human body, in which case the inventive optical measuring apparatus can measure blood distribution in the brain.

Further, in the optical measuring apparatus of the present invention, the light irradiation mechanism may includes: a condenser lens provided at the distal end of the optical fiber; a feed screw mechanism for controlling a distance between the condenser lens and the surface of the desired portion of the living body to be measured; and a piezoelectric element expandable or contractible in response to a voltage applied thereto so as to control an angular position of the condenser lens relative to the surface of the desired portion. Such arrangements can determine with high accuracy the distance between the condenser lens and the surface of the desired portion.

According to another aspect of the present invention, there is provided an optical measuring method for use with an optical measuring apparatus, which comprises: a step of moving, by means of a light-irradiation-mechanism control section, a light irradiation mechanism so that a light outputting end of the light irradiation mechanism gets closer to a desired portion of an object to be measured; a step of determining, on the basis of a distance value measured by a distance measuring section, whether the light outputting end of the light irradiation mechanism has reached a predetermined position near a surface of the desired portion; a step of irradiating near infrared light, emitted by a light source, to the desired portion of the object via the light outputting end of the light irradiation mechanism while, by means of a scanning mechanism, causing the light outputting end to make scanning movement relative to the surface of the desired portion; a step of removing a pulse wave detection signal representative of a pulse wave detected by a pulse wave detection section from a light detection signal representative of scattering reflected light detected by a light detection section; and a step of calculating, on the basis of the light detection signal having the pulse wave detection signal removed therefrom by the step of removing, a concentration of a biological substance present in the desired portion of the object to be measured.

According to still another aspect of the present invention, there is provided a program for causing a controlling computer of an optical measuring apparatus to perform an optical measuring process, which comprises the same steps or procedures as the above-mentioned optical measuring method.

BRIEF DESCRIPTION OF THE DRAWINGS

Certain preferred embodiments of the present invention will hereinafter be described in detail, by way of example only, with reference to the accompanying drawings, in which.

DETAILED DESCRIPTION OF THE PREFERRED EMBODIMENTS

Figure 1:
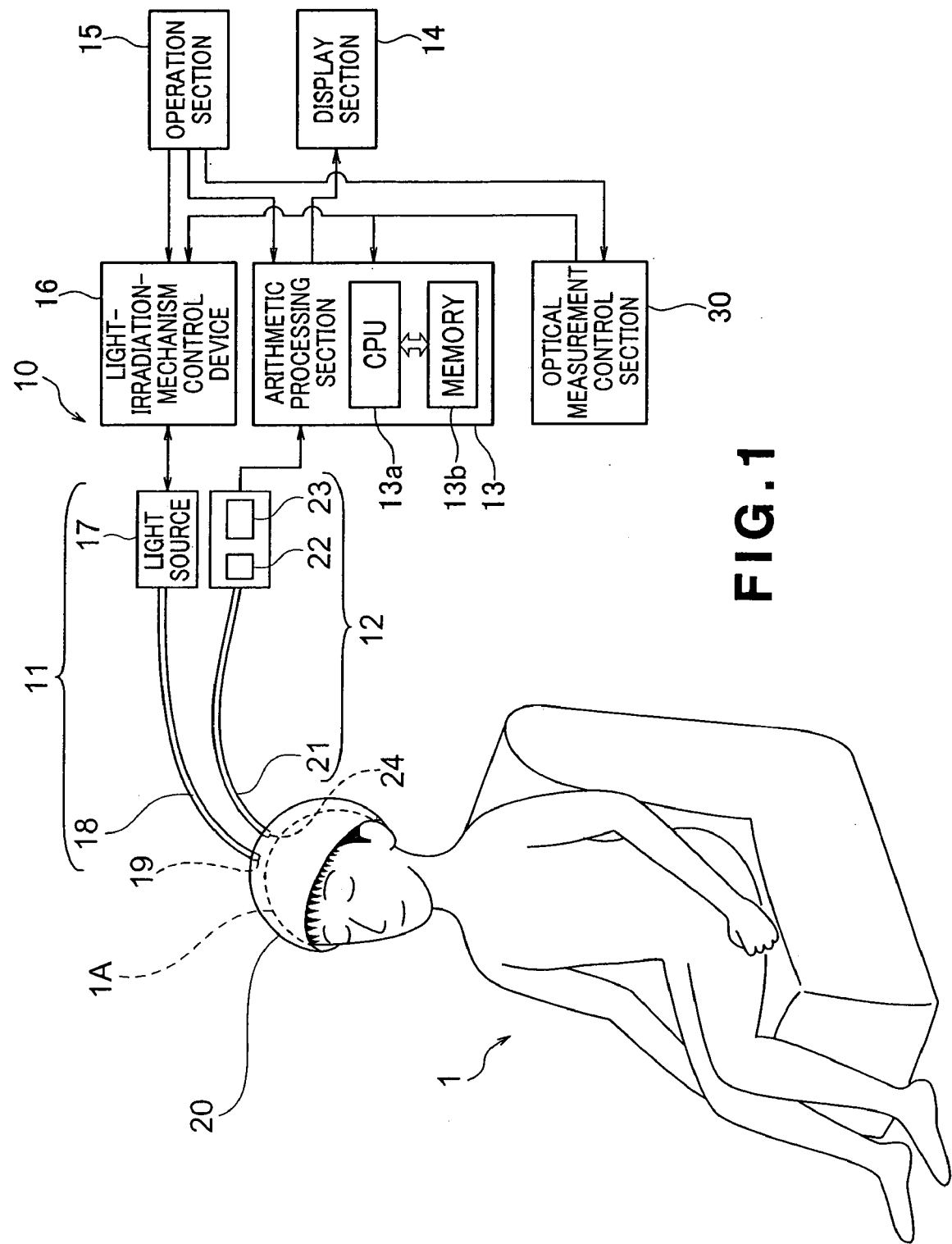
FIG. 1 is a view showing a general setup of an optical measuring apparatus in accordance with a first embodiment of the present invention, which also shows how the optical measuring apparatus is used.

Initial reference is made to FIG. 1 showing the general setup of an optical measuring apparatus in accordance with a first embodiment of the present invention. This optical measuring apparatus 10 includes a light irradiation mechanism 11, a light detection mechanism 12, an arithmetic processing section 13, a display section 14, an operation section 15, a light-irradiation-mechanism control device 16, and an optical measurement control section 30. The optical measurement control section 30 controls all measuring operations of the optical measuring apparatus 10.

The light irradiation mechanism 11 irradiates near infrared light to a desired portion 1A, such as a head, of a person (living body) to be measured 1. The light irradiation mechanism 11 includes a light source 17 emitting a plurality of light of different wavelengths in the near infrared range (i.e., near infrared light of different wavelengths), and an optical fiber 18 for passing therethrough the light emitted by the light source 17. The light source 17 may be in the form of a monochromatic light source, such as a semiconductor laser or light emitting diode, halogen lamp, tungsten lamp or other light source capable of outputting light of wavelengths in the near infrared range. In an alternative, light emitted by a light source having a continuous spectrum may be irradiated via a plurality of filters, such as interference filters each allowing light of a single wavelength to pass therethrough. In another alternative, the light source 17 may be one capable of emitting light of a plurality of single-wavelength light, or a monochromatic light source may be provided by passing light, emitted from a light source having a continuous spectrum, through a spectroscope.

In FIG. 1, only one optical fiber 18 is shown for simplicity. However, the light irradiation mechanism 11 may of course include a plurality of optical fibers for irradiating near infrared light, in which case desired measurement can be performed simultaneously for a plurality of spots on a desired portion of the head 1A. Ordinarily, a plurality of optical fibers are provided in order to perform measurement over a relatively great area of the head 1A of the to-be-measured person.

Figure 3:
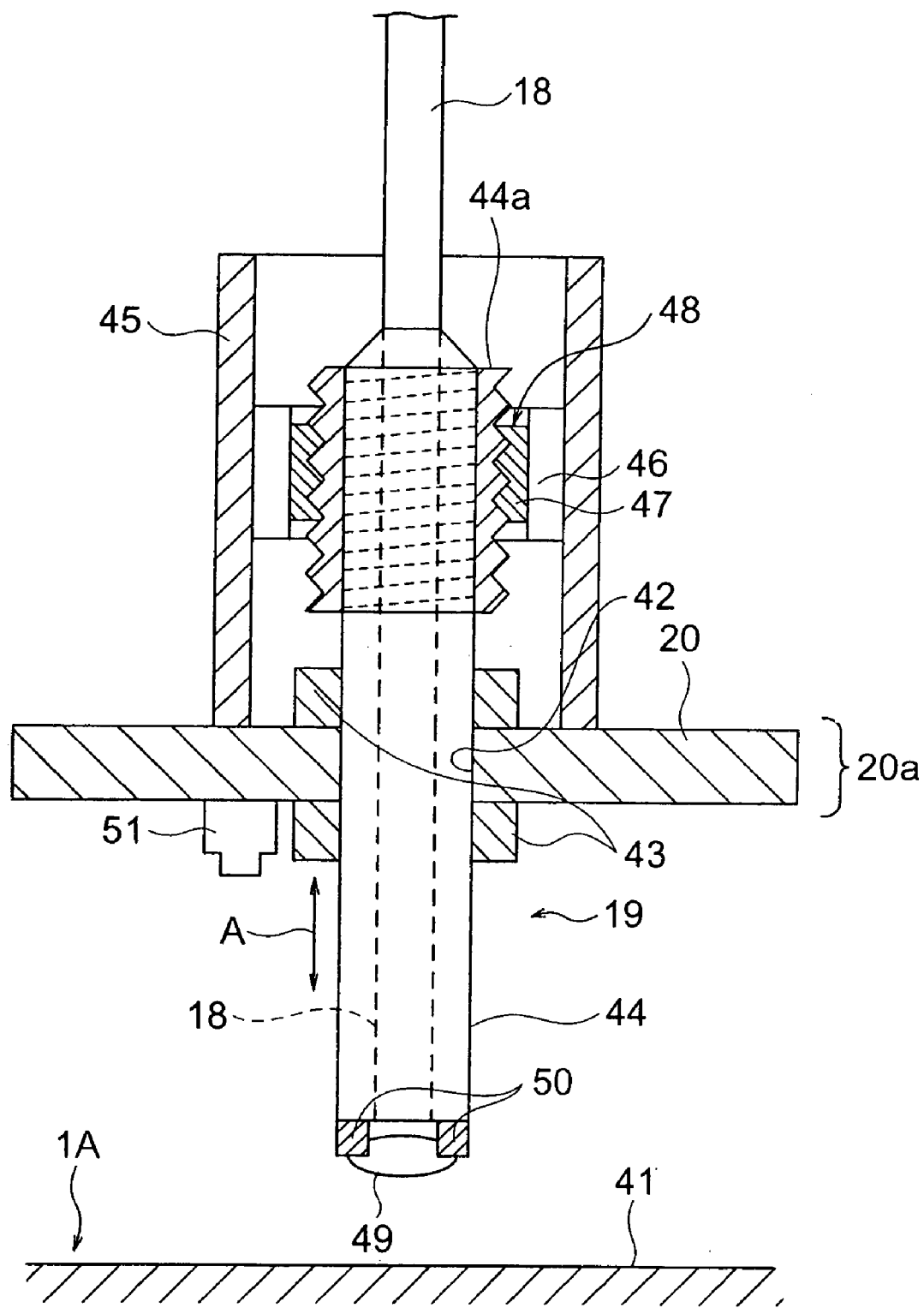
FIG. 3 is a vertical sectional view showing a light irradiation section provided on the helmet.

The optical fiber 18 is provided for irradiating therethrough the near infrared light from the light source 17 to the head 1A of the to-be-measured person 1. Specifically, the optical fiber 18 is connected at one end to the light source 17 and at the other end fixed to a helmet 20. The other end portion connected to the helmet 20 is constructed as the light irradiation section 19 as illustrated in FIG. 3.

The helmet 20 forms a cover member to which the light irradiation section 19 of the optical fiber 18 and a later-described optical fiber 21 of the light detection mechanism 12 are fixed. In other words, the helmet 20 is a unit for placing and holding the optical fiber 18 etc. of the optical measuring apparatus 10 in sufficient proximity to the measured portion of the head 1A and in fixed positional relation to the latter.

Note that the helmet 20 is shown in FIG. 1 merely conceptually and a specific form of the helmet 20 may be chosen as desired.

The light detection mechanism 12 includes the optical fiber 21 for collecting and transmitting the diffuse/scattering-based reflected light (commonly known as "arriving light") from the measured portion of the head 1A, a photo detector (e.g., photo diode or photoelectron multiplier) sensitive to a plurality of near infrared light of different wavelengths, and a signal processing section 23.

The optical fiber 21 is fixed at one end 24 to the helmet 20, and the end 24 is constructed as a light reception section. The light reception section 24 of the optical fiber 21 collects light scattering-reflected from the measured portion of the head 1A, and the collected light is output via the other end of the optical fiber 21 to enter the photo detector 22.

For simplicity of illustration and explanation, the light irradiation mechanism 11 and light detection mechanism 12 in the optical measuring apparatus 10 of FIG. 1 are each shown as employing only one optical fiber 18, 21 to provide a fundamental single-point light irradiation/reception structure. In practice, however, the light irradiation mechanism 11 and light detection mechanism 12 normally include a plurality of light irradiating optical fibers and light detecting optical fibers to provide multi-point light irradiation/reception (e.g., 24-point light irradiation/reception) structure, in order to measure blood distribution in a given portion of the head 1A. In the helmet 20, a measuring unit is constituted by the respective distal end portions of the light irradiating and light detecting optical fibers.

The signal processing section 23 of the light detection mechanism 12 converts the light, detected by the photo detector 22, into an electrical signal. The converted electrical signal is converted into a digital signal by an A/D converter (not shown) and then passed to the arithmetic processing section 13.

The arithmetic processing section 13, which comprises a computer including a CPU 13a and memory 13b, performs given arithmetic operations on data representative of the diffuse/scattering reflected light detected via the light detection mechanism 12, to thereby calculate blood distribution in the measured portion of the head 1A. Specifically, in the arithmetic processing section 13, the CPU 13a executes a signal processing program stored in the memory 13b and thereby calculates data representative of distribution of blood (and/or other biological substance) in the head 1A. The data representative of the blood distribution are sent to the display section 14, where the data are converted into image data and an image or graph indicating the blood distribution is visually shown.

The operation section 15 is an input means operable to make necessary settings and change a designated program and variable in the optical measuring apparatus 10. Via this operation section 15, the human operator can perform input operation to give necessary control instructions to the arithmetic processing section 13, light-irradiation-mechanism control device 16, optical measurement control section 30, etc.

On the basis of the instructions entered via the operation section 15, the light-irradiation-mechanism control device 16 performs intensity control, wavelength selection, etc. for the light emitted by the light source 17, or controls driving elements, such as piezoelectric elements, provided in the light irradiation section 19 of the optical fiber 18.

Figure 2:
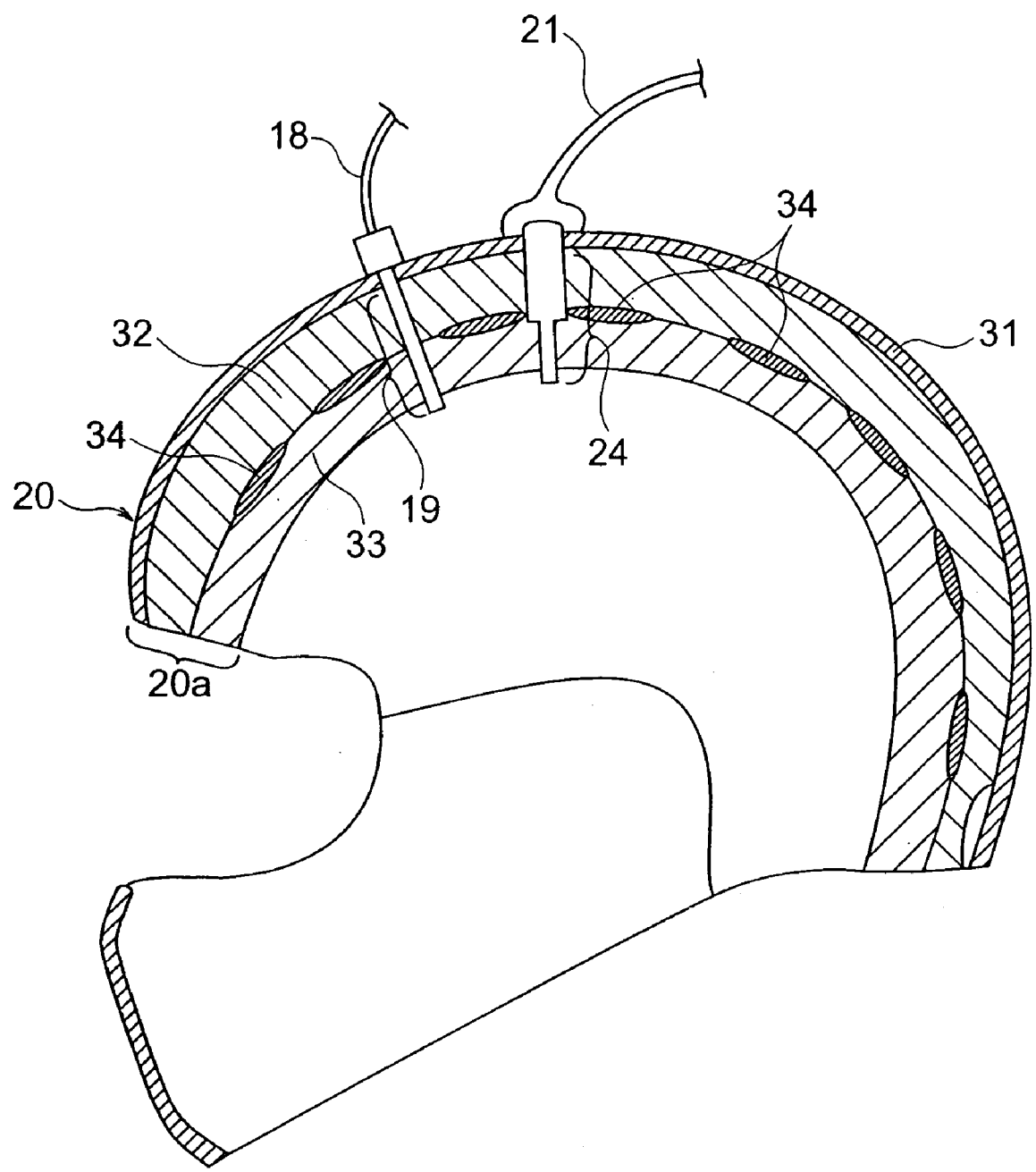
FIG. 2 is a vertical sectional view showing a detailed structure of a helmet employed in the optical measuring apparatus of FIG. 1.

Next, a description will be made about an example structure of the helmet 20 and an example manner in which the light irradiation section 19 and light reception section 24 are mounted on the helmet 20, with reference to FIG. 2 which shows more details of the helmet 20. Generally, the helmet 20 employed as the removably attachable cover member in the inventive apparatus is similar in shape to ordinary helmets for auto bicycles, although the helmet 20 in the optical measuring apparatus 10 may be of any desired shape other than that of the auto bicycle helmets. Namely, the helmet 20 may be formed into any desired shape corresponding to the shape of the object to be measured, such as the head 1A. External shell 20a of the helmet 20, as illustratively denoted in vertical section, includes an outer shell member 31 having a given strength, an outer liner 32, an inner liner 33, and a plurality of elastic members 34 interposed between the outer and inner liners 32 and 33. Note that FIG. 2 shows a thickness of the helmet external shell in a more or less exaggerative fashion. In fact, the helmet external shell 20a has a much smaller thickness as illustrated in FIG. 3, and the structure of the helmet 20 may be a simpler one.

The optical fiber 18 having the light irradiation section 19 and the optical fiber 21 having the light detection section 24 are fixed to the external shell 20a of the helmet 20. For example, the light irradiation section 19 and the light detection section 24 are provided in given positions of an apex region of the helmet 20. Detailed structure of the light irradiation section 19 will be later described with reference to FIG. 3. Optical fibers 18 and 21 forming the light irradiation section 19 and light detection section 24 have their respective distal end portions embedded in the external shell, and the respective distal end surfaces of the optical fibers 18 and 21 are exposed on the inner surface of the inner liner 33 to face the measured portion.

Only one light irradiating optical fiber 18 forming the light irradiation section 19 and only one light detecting optical fiber 21 forming the light detection section 24 are shown in FIG. 2 just as in FIG. 1; in practice, however, the optical measuring apparatus 10 of the present invention include a plurality of the light irradiating optical fibers 18 each forming the light irradiation section 19 and a plurality of the light detecting optical fibers 21 each forming the light detection section 24, as noted earlier. These optical fibers 18 forming the light irradiation sections 19 and optical fibers 21 forming the respective light detection sections 24 are properly arranged as a unit and fitted to the helmet 20 as the measuring unit.

When the helmet 20 constructed in the above-described manner is properly placed on the head 1A of the to-be-measured person 1 as shown in FIG. 1, there are normally formed gaps between the inner liner 33 and the head 1A due to the hair of the head 1A. When the helmet 20 is properly placed on the head 1A, the distal ends of the light irradiation sections 19 and light detection sections 24 are positioned a slight distance from the surface of the head 1A, i.e. positioned out of contact with the surface of the head 1A. Namely, in the state where the measuring unit on the helmet 20 of the inventive optical measuring apparatus 10 is duly attached to the head 1A, the distal ends of the light irradiation sections 19 and light detection sections 24 are never pressed into close contact with the skin of the head 1A. Thus, the to-be-measured person 1 will not have an uncomfortable feeling during the measurement by the optical measuring apparatus 10.

The following paragraphs describe an example detailed construction of the light irradiation section 19 that is provided at the end portion of the optical fiber 18 fitted to the helmet 20, with reference to FIG. 3.

FIG. 3 shows the helmet 20 when it is properly placed on the head 1A; no hair on the skin 41 of the head 1A is not illustrated for convenience of illustration. The light irradiation section 19 is fitted through a hole 42, formed across the thickness of the external shell 20a of the helmet 20, in such a manner that the irradiation section 19 is axially movable along the inner surface of the hole 42. Inner and outer ring-shaped guide members 43 are disposed around inner and outer opening ends of the hole 42. Specifically, the light irradiation section 19 includes an optical fiber guide/cover 44 passed through the central openings of the inner and outer ring-shaped guide members 43 and hole 42. The optical fiber guide/cover 44 has the distal end portion of the optical fiber 18 accommodated therein as denoted by dotted lines, and the guide/cover 44 with the optical fiber 18 fixed thereto is axially movable through the openings of the inner and outer ring-shaped guide members 43 and hole 42. The distal end surface (lower end surface in FIG. 3) of the optical fiber 18 is exposed on the lower end of the optical fiber guide/cover 44 to face the head skin 41. During the optical measurement performed by the apparatus, the distal end surface of the optical fiber 18 is held a slight distance from the head skin 41, i.e. out of contact with the head skin 41. With the measuring unit appropriately positioned like this, the desired optical measurement is carried out by causing near infrared light to be irradiated through the distal end surface of the optical fiber 18 to a desired portion of the head skin 41.

The optical fiber guide/cover 44 has a male thread portion 44a provided on the outer periphery of a proximal end portion (upper end portion in FIG. 3) thereof. Cylindrical member 45 is secured to the outer surface of the helmet's external shell 20a along the outer peripheral edge of the hole 42. The cylindrical member 45 is positioned in concentric relation to the optical fiber guide/cover 44. Ring-shaped motor 46 is fixed to the inner surface of the cylindrical member 45, and a gear 47 rotatable by the motor 46 is mounted on the inner surface of the motor 46. The inner gear 47 and male thread portion 44a, which are held in meshing engagement with each other, together constitute a feed screw mechanism 48. As the inner gear 47 is rotated in a given direction via the motor 46, the feed screw mechanism 48 can cause the optical fiber guide/cover 44, passed through the ring-shaped guides 43, to freely move in an axial direction A, so that the distance between the distal end surface of the optical fiber 18 and the surface of the head skin 41 can be adjusted as desired.

Figure 4:
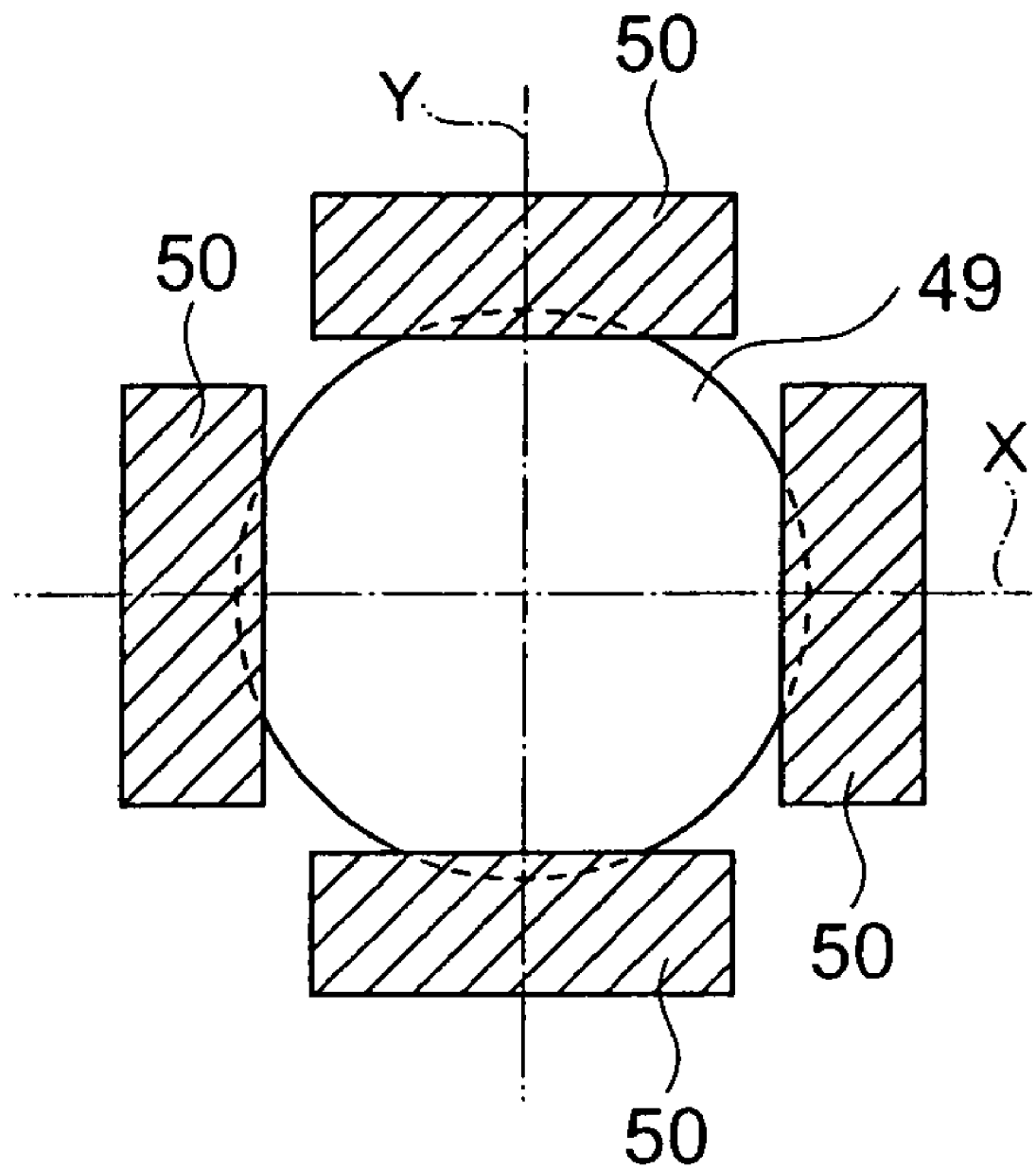
FIG. 4 is a bottom plan view of a portion of the light irradiation section where a condenser lens is mounted.

Condenser lens 49 is positioned at the distal end of the optical fiber guide/cover 44, and this condenser lens 49 is supported via a plurality of (e.g., four) piezoelectric elements 50 spaced apart from each other at uniform intervals along the circumference of the condenser lens 49. Each of the piezoelectric elements 50 is secured to the distal end surface of the optical fiber guide/cover 44. The condenser lens 49 collects the near infrared light output from the distal end surface of the optical fiber 18 so that the collected near infrared light is irradiated to the surface of the head skin 41. As seen in a bottom end view of FIG. 4, the condenser lens 49 is preferably supported by the piezoelectric elements 50 at four locations. Each of the piezoelectric elements 50 is generally in the shape of a rod and has a vertically (i.e., in the axial direction of the optical fiber 18) laminated structure. Given D.C. voltages or the like are applied to the piezoelectric elements 50, independently of each other, in the vertical direction of FIG. 3, so that the piezoelectric elements 50 can be expanded/contracted, independently of each other, in the vertical direction. Thus, by applying D.C. voltages to a pair of left and right piezoelectric elements 50 positioned on an X-axial line shown in FIG. 4, the condenser lens 49 can be inclined at an appropriate angle about a Y-axial line through expansion/contraction of the left and right piezoelectric elements 50. The remaining two piezoelectric elements (upper and lower piezoelectric elements in FIG. 4) 50 positioned on the Y-axial line can also be expanded/contracted, so that the condenser lens 49 can be inclined at an appropriate angle about the X-axial line through expansion/contraction of the piezoelectric elements 50. Further, by combining the inclining movement about the Y- and X-axis, the condenser lens 49 can be inclined with higher accuracy in predetermined directions over a predetermined angular range permitted by operating characteristics of the piezoelectric elements 50. Namely, the condenser lens 49 supported by the four piezoelectric elements 50 can be varied in its angular position or orientation over a desired angle and in a desired direction on the basis of the above-mentioned inclining movement. Speed of the orientation (angular position)-varying movement of the condenser lens 49 may be chosen as appropriate in accordance with expanding/contracting characteristics of the piezoelectric elements 50.

The orientation-varying movement of the condenser lens 49 can be controlled, for example, by controlling the respective intensity, application intervals, etc. of the voltages to be applied to the piezoelectric elements 50. Whereas an area of scanning, based on the orientation-varying movement of the condenser lens 49, is shown as a predetermined rectangular area, it may be of any other suitable shape. Irradiation range of the near infrared light in the instant embodiment is set as appropriate in accordance with characteristics of an area within the brain to be measured and piezoelectric elements 50, the numbers of the light irradiation and reception points, etc.

Whereas the light irradiation and reception are to be carried out at a plurality of points using a plurality of the condenser lens 49, the near-infrared-light irradiation ranges of adjoining the condenser lens 49 may be set in a more or less overcrowd manner so that enhanced measuring accuracy can be achieved for boundaries among the adjoining light irradiation areas on the head 1A.

If the light irradiation/reception is hindered by the head hair, accurate intra-brain measurement can not be achieved. With the arrangements of the present invention, however, it is possible to create a measuring environment free from influences of the head hair, to thereby permit accurate measurement. Namely, according to the present invention, the orientation-varying feature of the condenser lens 49 can increase the possibility for the irradiated near infrared light to reach a desired measured portion without being hindered by the head hair, thereby permitting high-accuracy optical measurement with increased efficiency. Because the light irradiation/reception having been influenced by the head hair can be easily identified, for example, on the basis of lower intensity of received light detection signals, data that are judged to be unsuitable for the accurate intra-brain measurement due to the influences of the head hair will be excluded from subsequent intra-brain data analysis.

Note that each of the piezoelectric elements 50 comprises, for example, a lamination of a piezoelectric ceramic material. In recent years, the piezoelectric ceramics with a piezoelectric effect have been attracting people's attention as medical micro machines. Where a piezoelectric element is applied as a drive source means, the element is often used in a high-frequency region. The piezoelectric effect of the piezoelectric element allows the element to function as a precision positioning element. Further, in the instant embodiment where the piezoelectric elements 50 are used as an actuator for the orientation-varying movement of the condenser lens 49, high excitation driving is carried out by applying high pulse voltages to the piezoelectric elements 50. The piezoelectric elements 50 can function as a small-size actuator having high-speed response, high displacement resolution and great rigidity.

Further, a distance measuring device 51 is provided on the inner surface of the external shell 20a of the helmet 20 adjacent to the optical fiber guide/cover 44. As the optical fiber guide/cover 44 is moved in the axial direction A, the distance measuring device 51 measures a distance between the inner surface of the helmet external shell 20a and the surface of the head skin, so that an amount of the axial movement of the optical fiber guide/cover 44 is adjusted with reference to the measured distance. Namely, the distance measuring device 51 is a device to be used for positioning the condenser lens 49 at the distal end of the optical fiber 18 so that the near infrared light is brought into focus on the measured body portion. The distance measurement by the distance measuring device 51 may be performed using the known laser ultrasonic measuring machine or ultrasonic measuring method.

Figure 5:
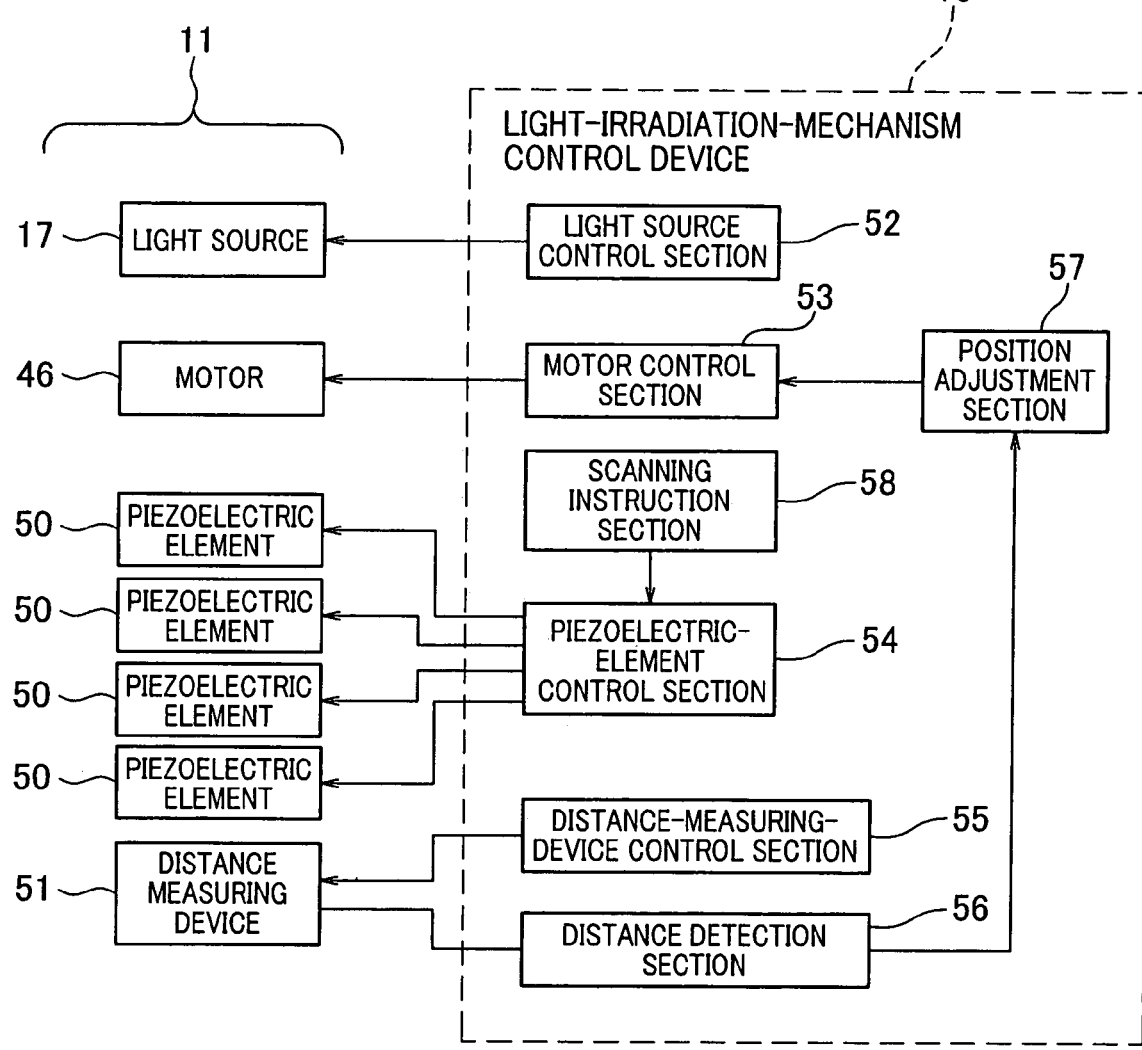
FIG. 5 is a block diagram showing an example structure of a light-irradiation-mechanism control device in the optical measuring apparatus.

As illustrated in FIG. 5, the above-mentioned light-irradiation-mechanism control device 16 performs control of the rotation of the motor 46 in the light irradiation section 19 of the light irradiation mechanism 11, expansion/contraction of the four piezoelectric elements 50 for varying the angular orientation of the condenser lens 49 and measuring operation of the distance measuring device 51, processing of measured data, etc.

More specifically, the light-irradiation-mechanism control device 16 includes a light source control section 52 for adjusting the output etc. of the light source 17, a motor control section 53 for controlling the rotation of the motor 46, a piezoelectric element control section 54 for controlling the expansion/contraction of the piezoelectric elements 50, and a distance-measuring-device control section 55 for controlling the measuring operation of the distance measuring device 51. Data representative of the distance obtained by the distance measuring device 51 is passed to a distance detection section 56. The motor control section 53 controls the motor 46 on the basis of a position-related instruction output from a position adjustment section 57 that determines a position to be controlled on the basis of the distance detected by the distance detection section 56. The piezoelectric element control section 54 receives a scanning instruction from a scanning instruction section 58, on the basis of which it controls the piezoelectric elements 50 so that the condenser lens 49 is varied in its angular position to perform scanning with the near infrared light.

Note that the light detection section 24 provided on the distal end portion of the optical fiber 21 in the light detection mechanism 12 is secured to the external shell 20a of the helmet 20.

The helmet 20 has been described above as having only one light radiation section 19 and only one light reception section 24 provided therein for convenience of explanation; in practice, however, a plurality of (eight in the instant embodiment) light radiation sections 19 and light reception sections 24 are provided in the helmet 20 as the measuring unit 60, as set forth above.

Figure 6:
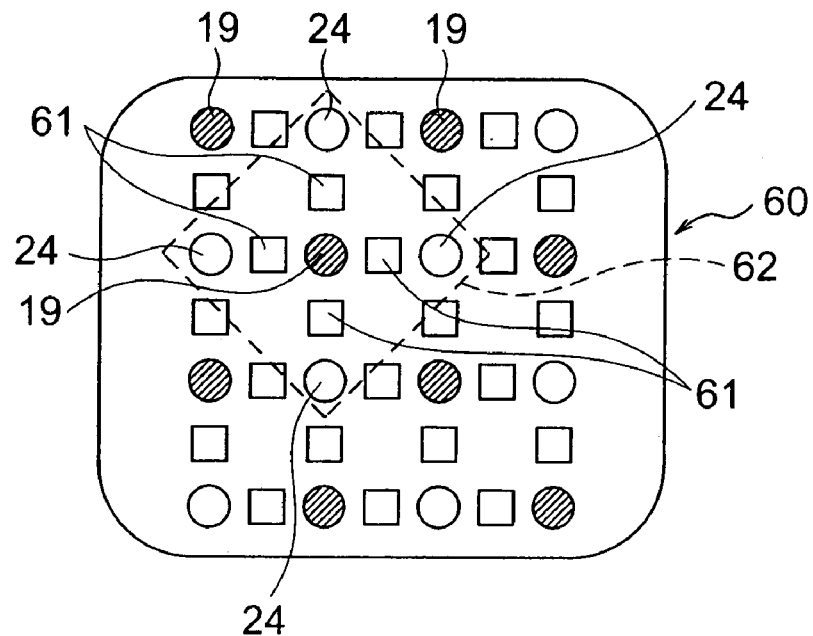
FIG. 6 is a diagram showing an example arrangement or layout pattern of light radiation sections and light reception sections in a measuring unit provided on the helmet.

FIG. 6 shows an example arrangement pattern of the eight light radiation sections 19 and light reception sections 24. Specifically, FIG. 6 shows the predetermined inner surface area of the helmet 20 where the light radiation sections 19 and light reception sections 24 are arranged, as projected, for example, onto the surface of the skin of the head 1A.

Figure 7:
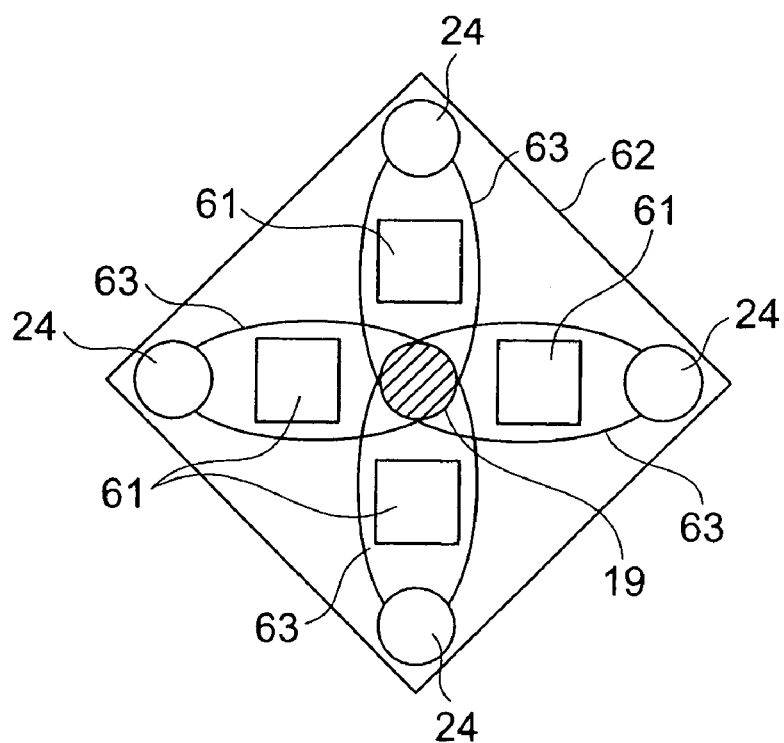
FIG. 7 is a diagram showing relationship among one of the light irradiation sections, light reception sections surrounding the one light irradiation section and a desired portion of an object to be measured.

In the figure, reference numeral 60 represents the measuring unit, and each hatched circle represents the position of one of the light irradiation sections 19 while each non-hatched circle represents the position of one of the light reception sections 24. Each square 61 between the hatched and non-hatched circles represents a measured spot of the head 1A. FIG. 7 is a fragmentary view showing in enlarged scale an area 62 denoted by dotted lines in FIG. 6. As shown in FIG. 7, four measured spots 61 are formed around each of the light irradiation section 19 in conjunction with the light reception sections 24 positioned around the light irradiation section 19. Further, each region 63 depicted among the four light reception sections 24 positioned around the light irradiation section 19 is where the near infrared light from the light irradiation section 19 is irradiated to the head 1A, reflected from the measured spot and then received by the corresponding light reception section 24.

As clear from the foregoing description, and particularly seen in FIG. 6, a total of 24 measured spots 61 are set by the measuring unit 60 including eight light irradiation section 19 and eight light reception section 24.

Figure 8:
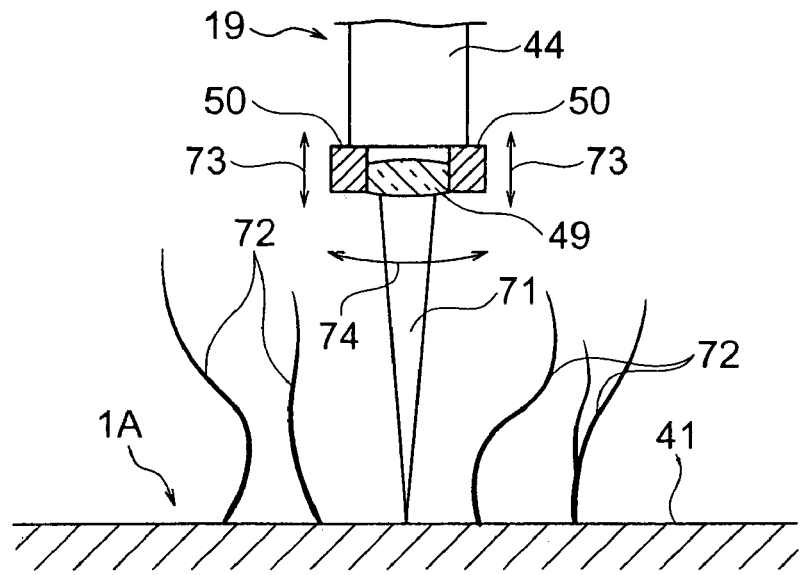
FIG. 8 is a view explanatory of scanning with near infrared light irradiated from the light irradiation section.

Now, a description will be made about the scanning with the output near infrared light from the light irradiation section 19. The near infrared red light 71 output from the distal end surface of the optical fiber 18 in the optical fiber guide/cover 44 is collected by the condenser lens 49 and then irradiated to the head 1A with the focus on the head skin 41. Because hair 72 exists on the head skin 41, the near infrared light 71 would normally be hindered by the hair 72 before reaching the skin 41. Thus, during the optical measurement, the expansion/contraction of selected two of the piezoelectric elements 50, as shown in FIG. 8, is controlled as appropriate to vary the angular position or orientation of the condenser lens 49 so as to deflect the near infrared light 71 for scanning of the measured portion. In this way, an appropriate measuring environment can be provided where the near infrared light 71 can be irradiated to the head skin 41 without hindrance by the hair 72.

Figure 9:
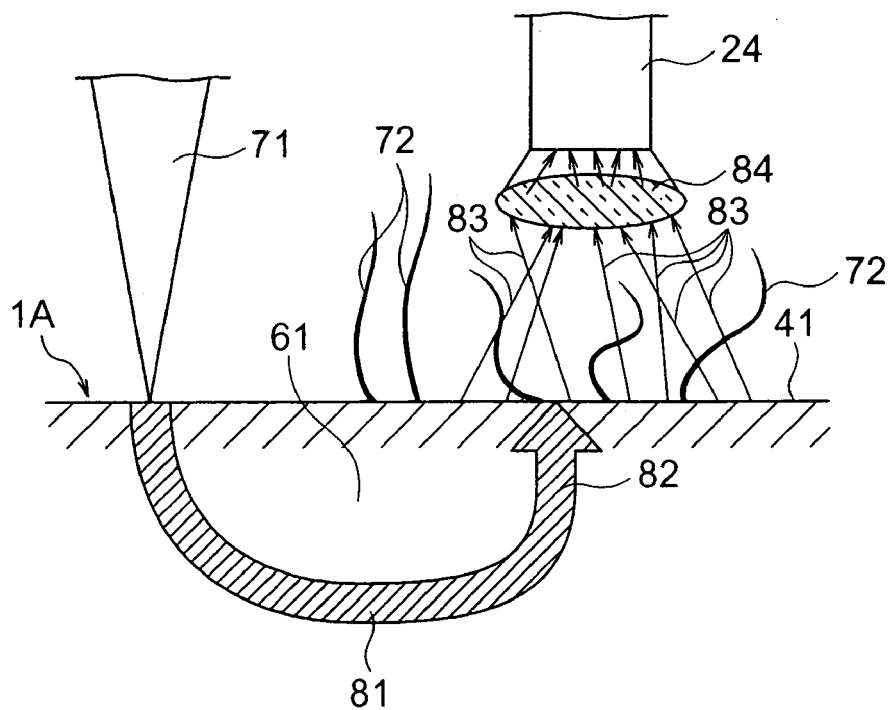
FIG. 9 is a view explanatory of scattering reflection of the near infrared light irradiated to the desired portion of the object to be measured.

As illustrated in FIG. 9, the near infrared light 71 directly irradiated to the surface of the head skin 1A without being hindered by the head hair 72 enters the surface layer of the head 1A, and then scattered within the surface layer. In FIG. 9, reference numeral 81 represents a region where the near infrared light 71 scatters within the surface layer. The thus-scattered near infrared light 71 then gets out of the head skin 41 as depicted by arrows 82 and 83, and then reaches the light receiving end surface of the light reception section 24 via a condenser lens 84. Brain tissue area including the scattering region 81 and regions in the neighborhood of the scattering region 81 constitutes the above-mentioned measured spot 61 of the head 1A.

Figure 10:
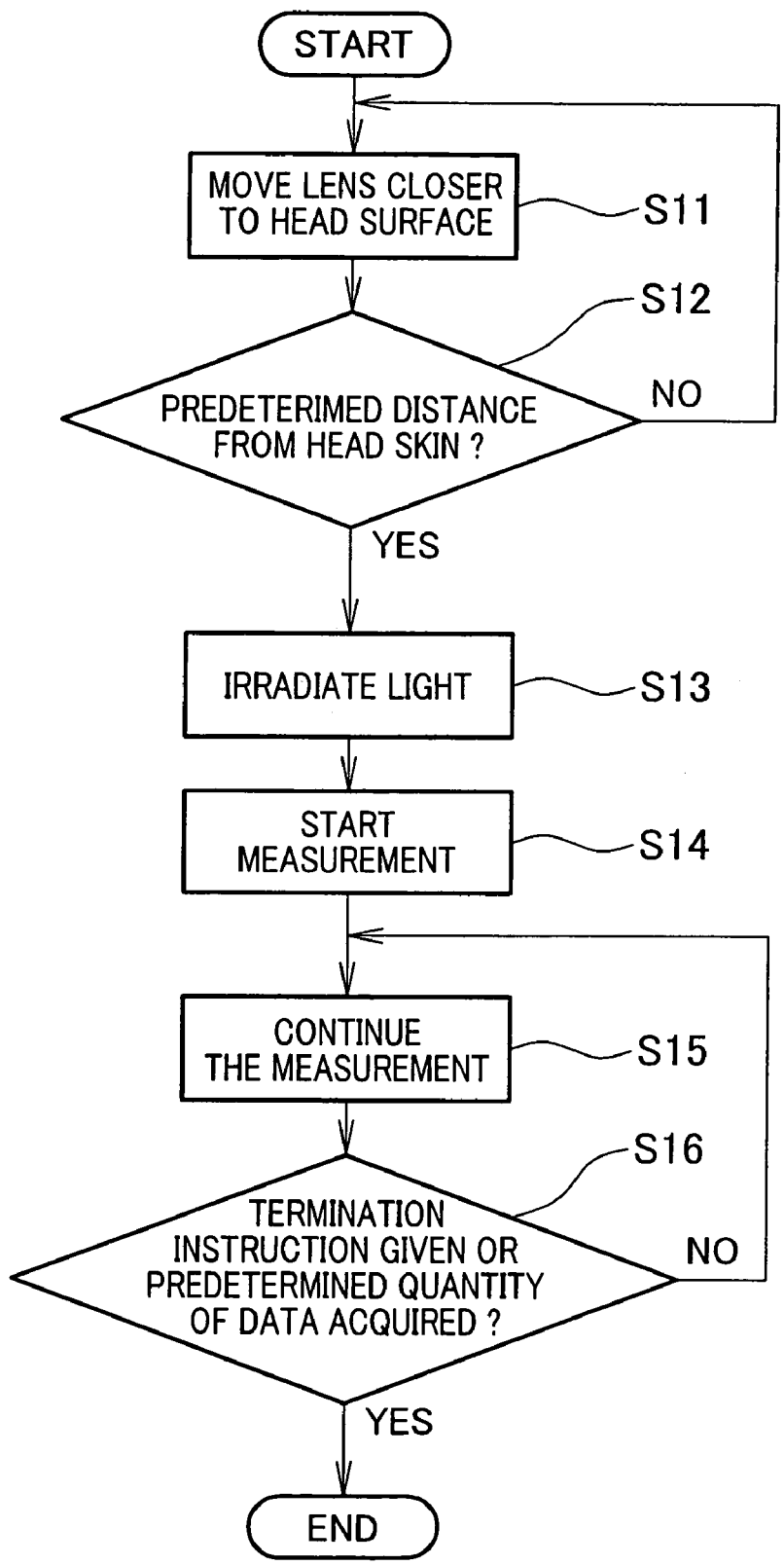
FIG. 10 is a flow chart showing a sequence of optical measurement performed in the first embodiment of the optical measuring apparatus.

Next, behavior of the optical measuring apparatus 10 will be described. All the measuring operations of the optical measuring apparatus 10 are controlled by the above-mentioned optical measurement control section 30 in accordance with a measuring program stored in a memory of the control section 30. FIG. 10 is a flow chart explanatory of measuring control performed in accordance with the measuring program.

Prior to initiation of the measurement by the optical measuring apparatus 10, the helmet 20 is placed on the head 1A of the to-be-measured person 1 as illustratively shown in FIG. 1. When the helmet 20 has been duly placed on and attached to the head 1A, each of the light irradiation sections 19 and light reception sections 24 of the measuring unit 60 on the inner side of the helmet 20 is positioned out of contact with the head skin 41.

Then, at step S11 of FIG. 10, the condenser lens 49 is moved closer to the head 1A. For this purpose, each of the light irradiation sections 19 moves the optical fiber 18 (and hence the condenser lens 49 at the distal end of the fiber 18) closer to the surface of the head 1A by driving the motor 46 on the basis of distance data obtained by the distance measuring device 51 while determining, at step S12, whether a predetermined focusing condition is satisfied or not. Once the predetermined focusing condition has been satisfied, i.e. the distance measured by the distance measuring device 51 has reached a predetermined value, as determined at step S12, the movement, toward the surface of the head 1A, of the condenser lens 49 is terminated, and the control proceeds to step S13.

At next step S13, the light source 17 etc. are driven to emit near infrared light under the control of the light-irradiation-mechanism control device 16, so that each of the light irradiation sections 19 irradiates the near infrared light to a predetermined one of the measured spots on the head surface. For appropriate irradiation of the near infrared light 71, the four piezoelectric elements 50 are controlled to expand or contract as appropriate, so that the near infrared light 71 irradiated in the focused condition can be deflected to scan a predetermined range.

When the near infrared light is irradiated to the predetermined measured spot of the head 1A, reflection of the scattering light 83 occurs in a brain tissue of the measured spot in accordance with blood distribution therein, so that the scattering light 83 is received by the light receiving surface of the light reception section 24. Under such conditions, the optical measurement is initiated and continued at steps S14 and S15. The optical measurement is continued until a predetermined measurement termination condition is met at step S16. The measurement termination condition is that a termination instruction has been given by the measuring operator or that a predetermined quantity of data has been acquired through the measurement. Upon satisfaction of the measurement termination condition, the optical measurement is brought to an end.

The scattering reflected light, having passed through the brain tissue and detected by the light detection mechanism 12 including the light reception section 24, is then subjected to an analysis process by the arithmetic operation section 13. In the analysis process, a signal processing program stored in the memory 13b is executed for processing signals in synchronism with the orientation-varying movement of the condenser lens 49, i.e., scanning movement of the near infrared light 71 and performing an analysis using signals based on the scattering reflected light components of the near infrared light 71 irradiated without hindrance by the head hair 72. Through the analysis of the reflected light, information about an activation state of the brain tissue is obtained on the basis of information representative of a blood distribution state detected through the optical measurement. The activation state of the brain tissue in the measured portion is visually presented on the display section 14.

Note that the activated portion of the brain tissue has a particular characteristic that an increased amount of blood flows in blood vessels in the brain tissue. Thus, by acquiring information about the blood distribution utilizing the particular characteristic, it can be known which portion within the cerebrum is currently activated. The near infrared light in the 0.75–2.5 μm wavelength range presents a high rate of transmission through a living body and passes through the head skin and skull into the cerebral cortex. Further, because the hemoglobin in blood presents a different rate of near infrared light absorption depending on whether it is of an oxygenated type or deoxygenated type, blood amount and distribution of the two types of hemoglobin in the cerebral cortex can be acquired by analysis of the scattering reflected light of the near infrared light irradiated to the head. Therefore, it is possible to investigate the activation state and function of the cerebrum by the inventive optical measuring apparatus analyzing the scattering reflection of the near infrared light.

Because the measuring unit 60 can be properly attached to the head 1A by just placing the helmet 20 on the head 1A, the instant embodiment can minimize the necessary preparing operations for the optical measurement and overall time and labor required for the optical measurement. Also, since the distal ends of probe elements, such as the light irradiation sections, provided in the measuring unit need not be placed in contact with the head or the like, the instant embodiment can minimize physical and psychological loads on the to-be-measured person. Further, when the measuring unit 60 is to be attached to the head or other desired body portion of the to-be-measured person, just placing the helmet 20 on the head 1A can appropriately fix the measuring unit 60 in position, so that undesired displacement of the light irradiation and detection sections can be reliably avoided to thereby provide accurate measured results.

Furthermore, the above-described embodiment, where the near infrared light irradiated to each of the measured spots is deflectable or variable in desired directions, instead of being fixed in its irradiation direction, to increase the scanning range of the measured spot, can acquire measurement information for a wider area of the desired body portion. In addition, because the near infrared light thus deflected can be irradiated directly to the measured spot without hindrance by the hair etc., the instant embodiment can reduce the necessary power of the near infrared light to be used.

Figure 11:
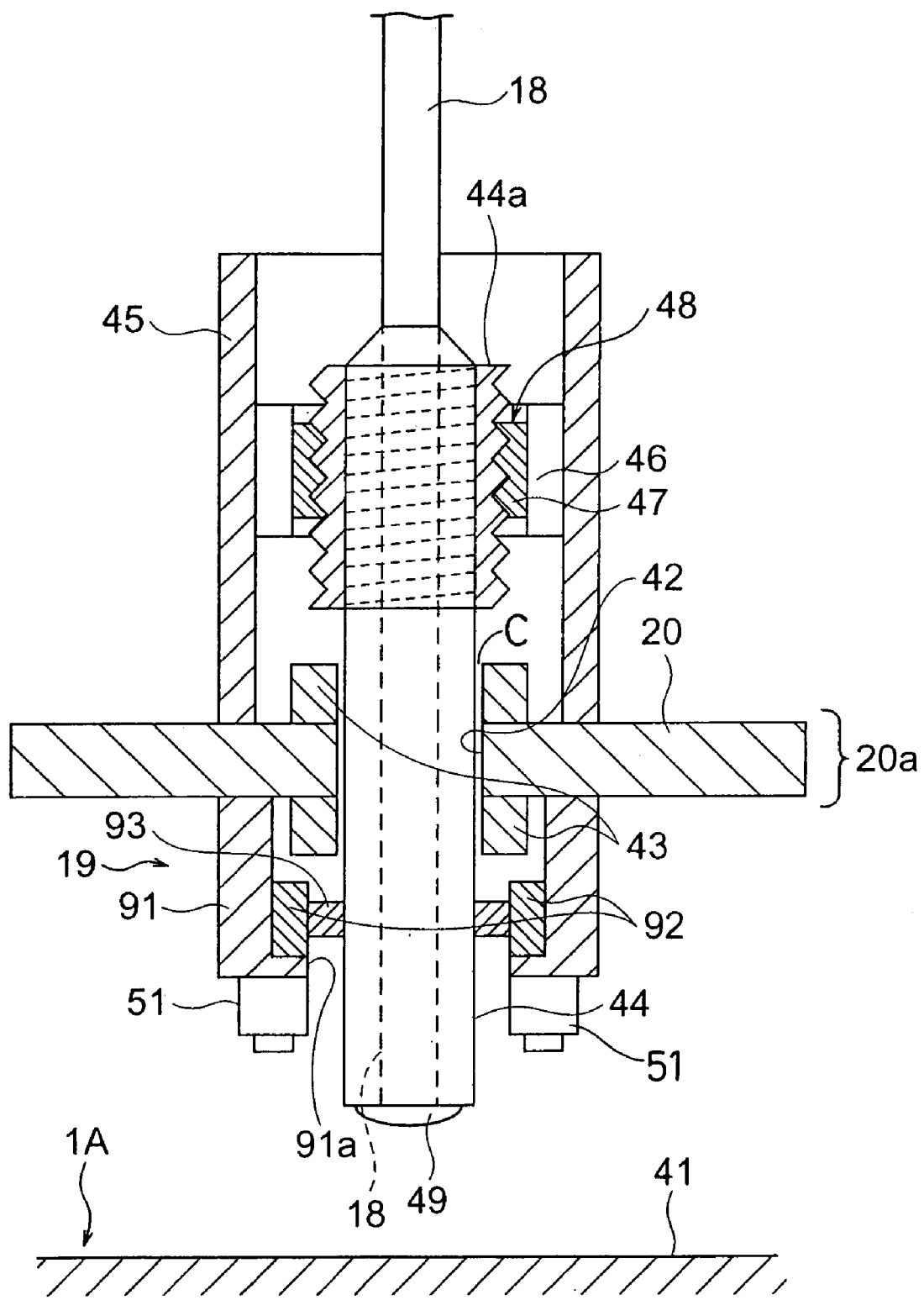
FIG. 11 is a vertical sectional view showing another embodiment of the light irradiation section.

The following paragraphs describe another embodiment of the light irradiation section 19, with reference to FIG. 11 where substantially the same elements as in FIG. 3 are represented by the same reference characters. Detailed description of the same elements as in FIG. 3 are omitted here, and only different portions from those of FIG. 3 will be described.

In the light irradiation section 19 of FIG. 11, a cylindrical portion 91 is secured to the inner surface of the helmet's external shell 20a around the inner guide member 43. The optical fiber guide/cover 44 is supported in an opening 91a of the cylindrical portion 91 via a ring-shaped guide member 93 using a plurality of (e.g., four) piezoelectric elements 92.

The optical fiber guide/cover 44, as set forth earlier, is fitted through the hole 42, formed across the thickness of the inner guide member 43, and central holes of the inner and outer ring-shaped guide members 43 in such a manner that the guide/cover 44 is axially movable along the holes. Given clearance C is formed between the outer peripheral surface of the optical fiber guide/cover 44 and the inner peripheral surfaces of the helmet's external shell 20a and guide members 43 defining the above-mentioned holes, so that a lower portion of the guide/cover 44 is displaceable or bendable in a diametric direction thereof. Each of the piezoelectric elements 92 disposed between lower portions of the cylindrical portion 91 and optical fiber guide/cover 44 is capable of expanding or contracting in a horizontal direction in response to a given voltage applied thereto.

For example, the expansion/contraction of the two (i.e., left and right) piezoelectric elements 92 shown in FIG. 11 is controlled such that, if one of the piezoelectric elements 92 expands, the other piezoelectric element 92 contracts. Thus, the lower portion of the optical fiber guide/cover 44 is displaceable horizontally, i.e. in the left-and-right direction of FIG. 11. Similarly, with expansion/contraction of the other two piezoelectric elements 92 (not visible in the figure) disposed perpendicularly to the sheet of the figure, the lower portion of the optical fiber guide/cover 44 is displaceable in a direction perpendicular to the sheet of the figure. By combining the displacement of the piezoelectric elements 92 in the left-and-right direction and direction perpendicular to the sheet of the figure, a condenser lens 49 disposed at the distal end of the optical fiber guide/cover 44 can be oriented in a desired direction. Note that the optical fiber guide/cover 44 is formed of an appropriate elastic or flexible material to permit the orientation-varying movement of the condenser lens 49 through the expansion/contraction of the piezoelectric elements 92 responsive to the applied voltages.

In the embodiment of FIG. 11, the condenser lens 49 is fixed to the distal end surface (lower end surface in FIG. 11) of the optical fiber guide/cover 44, and thus the condenser lens 49 itself does not move relative to the surface of the measured portion.

Further, at least one distance measuring device 51 is secured to the distal end surface of the cylindrical portion 91. In this embodiment of the light irradiation section 19, the distance measuring device 51 is positioned closer to the skin 41 of the head 1A than the counterpart of FIG. 3.

In the light irradiation section 19 thus arranged, the lower portion of the optical fiber guide/cover 44 itself is displaceable to deflect the near infrared light, emitted from the distal end surface of the optical fiber 18, for optical scanning.

Figure 12:
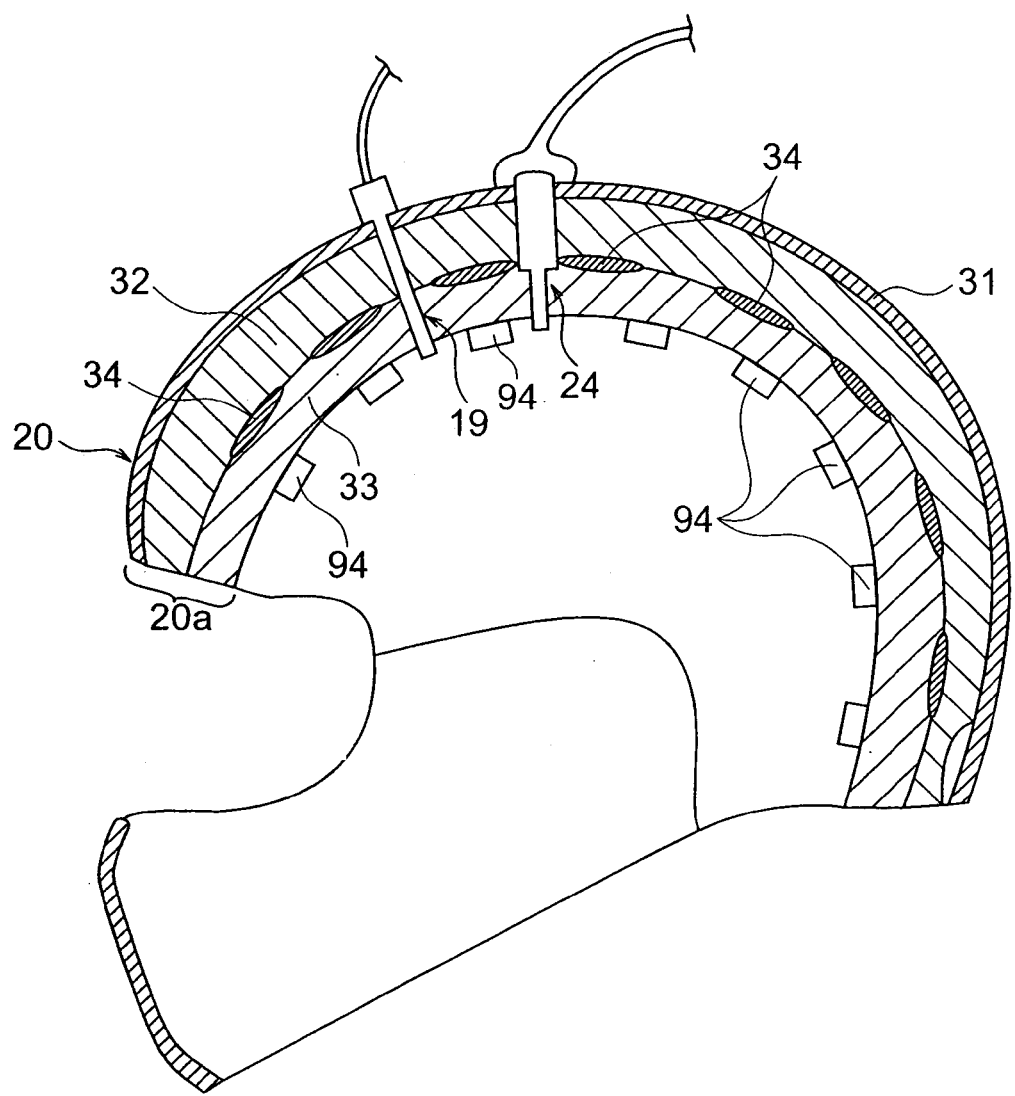
FIG. 12 is a view showing a modified embodiment of the helmet.

FIG. 12 is a modified embodiment of the helmet 20, where substantially the same elements as in FIG. 2 are represented by the same reference characters and detailed description of the same elements are omitted here to avoid unnecessary duplication. This modified embodiment of the helmet 20 is different from the embodiment of FIG. 2 in that a plurality of projections 94 are provided on the inner surface of the inner liner 33. By virtue of the provision of the projections 94 in the helmet 20, it is possible to even more reliably prevent the distal ends of the light irradiation section 19 and light reception section 24 of the measuring, unit from directing contacting the skin of the head 1A.

Figure 13:
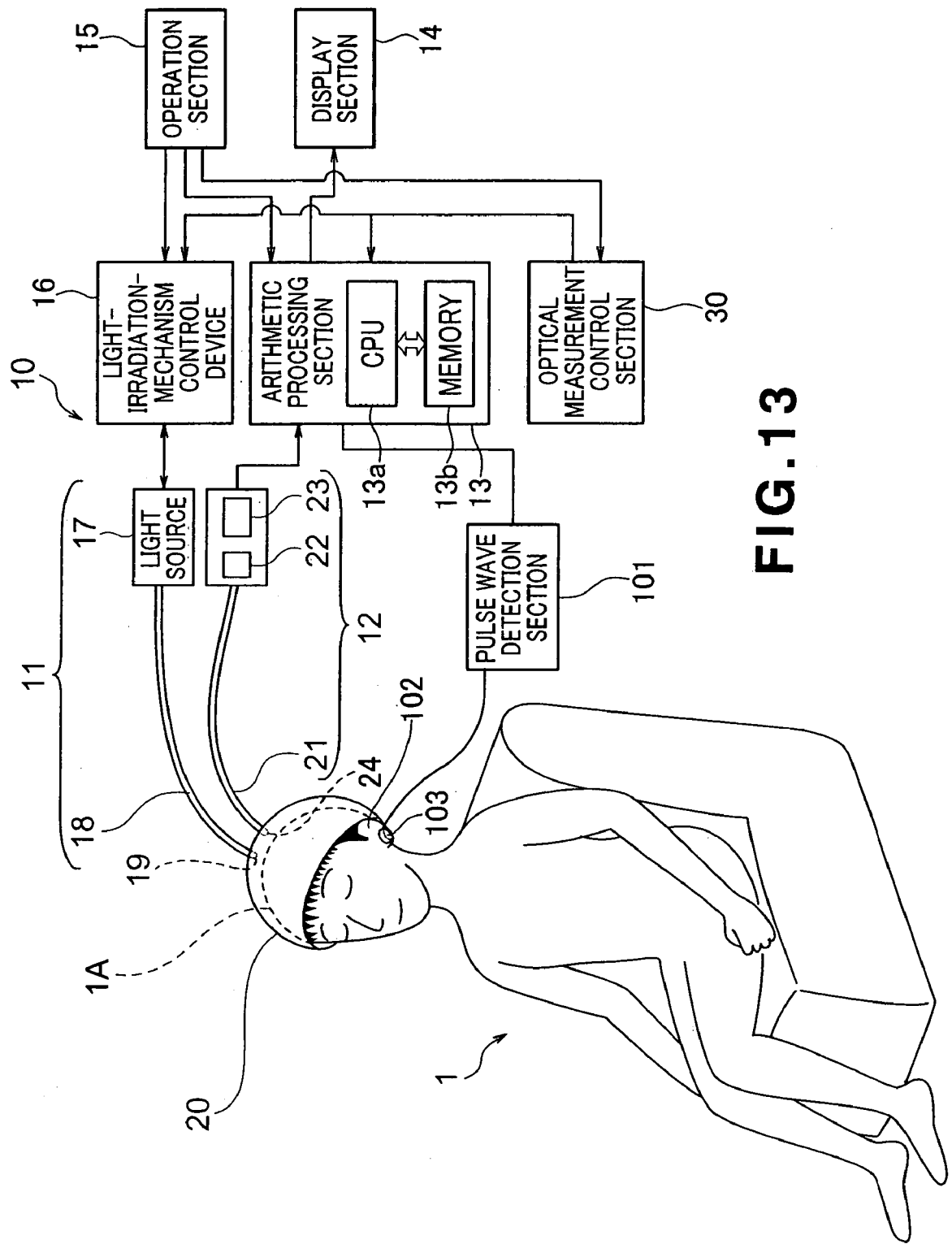
FIG. 13 is a view showing a general setup of an optical measuring apparatus in accordance with a second embodiment of the present invention, which also shows how the optical measuring apparatus is used.

Next, a description will be made about an optical measuring apparatus in accordance with a second embodiment of the present invention, with reference to FIGS. 13–17. The second embodiment of the optical measuring apparatus 10 is characterized by being constructed to provide more accurate optical measurements. FIG. 13 is similar to FIG. 1, where substantially the same elements as in FIG. 2 are represented by the same reference characters. Fundamental setup of the second embodiment is similar to that already described above in relation to the first embodiment and therefore will not be described here to avoid unnecessary duplication.

The second embodiment of the optical measuring apparatus 10 includes a light irradiation mechanism 11, a light detection mechanism 12, an arithmetic processing section 13, a display section 14, an operation section 15, alight-irradiation-mechanism control device 16, an optical measurement control section 30, and a pulse wave detection section 101. Structures and functions of the light irradiation mechanism 11, light detection mechanism 12, arithmetic processing section 13, display section 14, operation section 15, light-irradiation-mechanism control device 16 and optical measurement control section 30 in the second embodiment are similar to those already described above in relation to the first embodiment.

The pulse wave detection section 101 is provided for detecting a pulse wave (i.e., acquiring pulse wave data) from another or auxiliary predetermined body portion 102 separate from the principal body portion measured by the light detection mechanism 12. FIG. 13 shows an example where pulse wave data are acquired from an earlobe 102. Pulse wave sensor 103 is attached to the earlobe 102 for acquiring pulse wave data from a to-be-measured living body 1. The instant embodiment 10 is constructed to eliminate pulse wave noise produced by pulsation of arteries as set forth previously in relation to FIG. 18, to thereby detect blood distribution in the measured portion with a higher accuracy. For this purpose, it is preferable that the pulse wave sensor 103 be attached to such a body portion where pulse wave data similar to those acquired from the arteries 208 can be acquired. For example, the pulse wave sensor 103 is attached to a body portion, such as the earlobe, near the principal measured portion covered by the light detection mechanism 12, or a body portion located substantially the same distance from the heart as the principal measured portion.

The pulse wave data acquired by the pulse wave detection section 101 are passed to and stored in the arithmetic processing section 13.

The following paragraphs explain the basic principles of the optical measurement by the optical measuring apparatus 10 of the present invention, in relation to a case where a state of blood distribution in the brain is to be detected.

Because, in general, an increased amount of blood flows in an activated portion in the brain, investigating distribution of blood can tell which portion in the brain is working actively. The near infrared light in the 750 nm–2,500 nm wavelength range presents a high rate of transmission through a living body and efficiently passes through the head skin and skull into the cerebral cortex. Further, because the hemoglobin in blood presents a different rate of near infrared light absorption depending on whether it is of the oxygenated type or deoxygenated type, blood amount and distribution of the two types of hemoglobin in the cerebral cortex can be acquired by analysis of the scattering reflection of the near infrared light irradiated to the head. Therefore, it is possible to study, investigate or test the activation state and function of the cerebrum by the inventive optical measuring apparatus 10 analyzing the scattering reflection of the near infrared light.

Heretofore, the fMRI (functional Magnetic Resonance Imaging) technique etc. have been used for study of the cerebrum. However, the fMRI technique has not been satisfactory in that it is very expensive and requires large-scale equipment. By contrast, the optical measuring apparatus 10 of the present invention can accomplish various advantageous benefits; for example, it can readily perform desired measurement with simple facilities, reduce loads on a to-be-measured person, reduce necessary costs and achieve enhanced safety. Further, whereas the fMRI technique can only measure deoxygenated hemoglobin, the optical measuring apparatus 10 of the present invention can measure both oxygenated hemoglobin and deoxygenated hemoglobin.

Figure 14:
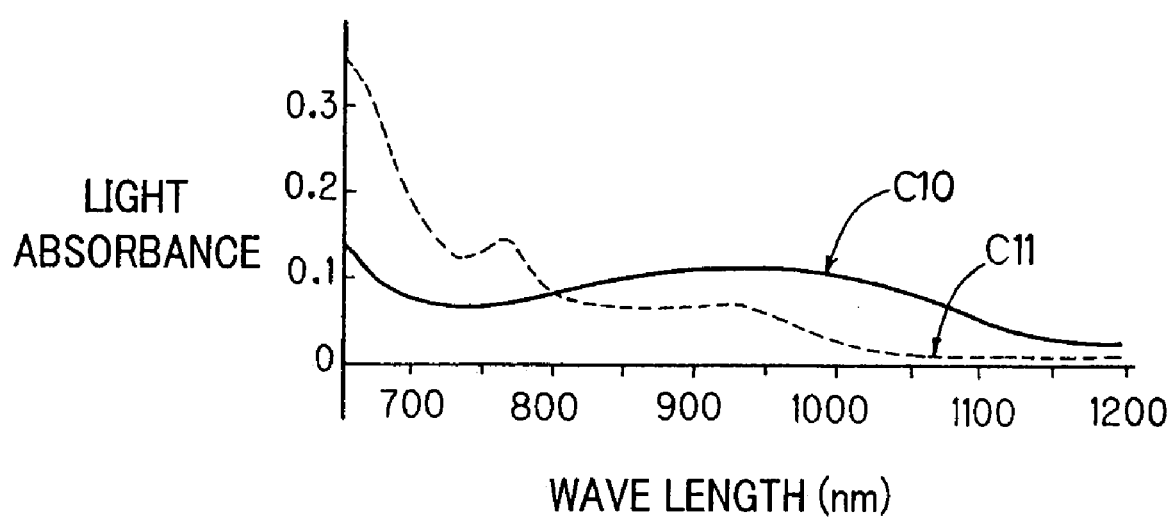
FIG. 14 is a graph showing an absorption spectrum of hemoglobin in blood.

Principles on which the concentration of hemoglobin is measured are explained below on the basis of a reference literature ("Nippon Bunko Gakkai Sokuteiho Series 32, Near Infrared Light Spectroscopy Method", Compiled by Yukihiro Ozaki and Satoshi Kawada, Gakkai Shuppan Center, First Edition, May 20, 1996). FIG. 14 is a graph showing an absorption spectrum of hemoglobin in blood. In FIG. 14, the horizontal axis represents a light wavelength in the near infrared range, while the vertical axis represents a light absorbance. Curve C10 indicates an absorption spectrum of oxygenated hemoglobin, and a curve C11 indicates an absorption spectrum of deoxygenated hemoglobin. The oxygenated hemoglobin presents a gentle absorption peak at a 930 nm wavelength, while the deoxygenated hemoglobin presents absorption peaks at 760 nm and 905 nm wavelengths. Namely, the oxygenated hemoglobin and deoxygenated hemoglobin present different absorption spectra.

For a scattering-type object to be measured having multiple components (i), such as a living body, the Lambert-Beer law generally established with a transparent sample may be expressed by Mathematical Expression (1) below.

$$\log(I_o(\lambda)/I(\lambda)) = \Sigma k_i(\lambda) \cdot C_i \quad \text{Mathematical Expression (1)},$$

where $I_o(\lambda)$ represents the intensity of incident light of a wavelength $\lambda$, $I(\lambda)$ represents the intensity of scattering reflected light and $C_i$ represents the concentration of a component (i). In many cases, the constant $k_i$ may be obtained empirically with an actual tissue using an absorption coefficient and scattering correction term.

The concentrations $C_i$ of the individual components can be determined by simultaneously evaluating Mathematical Expression (1) with three or four wavelengths and solving simultaneous equations. For example, in order to obtain the concentrations of oxygenated hemoglobin, deoxygenated hemoglobin and all the hemoglobin, three near infrared light of 780 nm, 805 nm and 830 nm wavelengths may be irradiated, and then simultaneous equations derived from Mathematical Expression (1) may be solved. Because the amounts of oxygenated and deoxygenated hemoglobin and blood vary over time in an actual living body tissue, it is necessary to perform simultaneous measurement using three or more kinds of light of different wavelengths as noted above. However, near infrared light of any other suitable wavelengths than the above-mentioned 780 nm, 805 nm and 830 nm may be used.

Figure 15A:
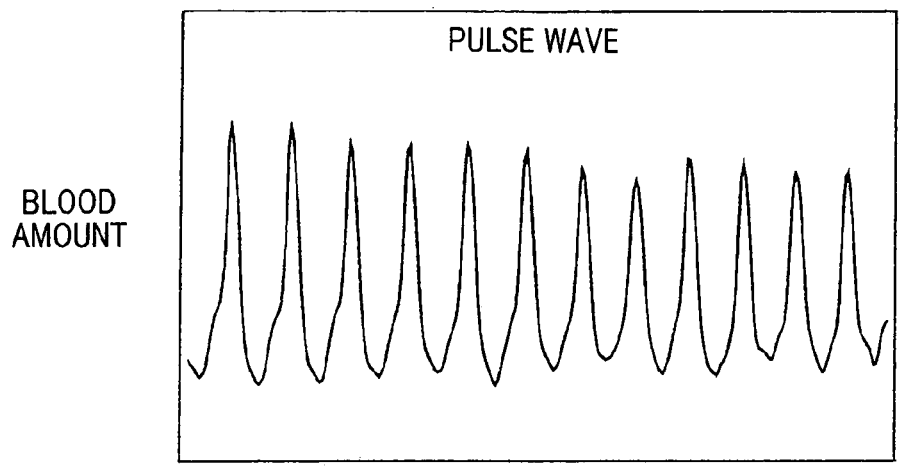
FIG. 15A is a waveform diagram of a signal indicative of blood amount variation corresponding to a pulse wave.
Figure 15B:
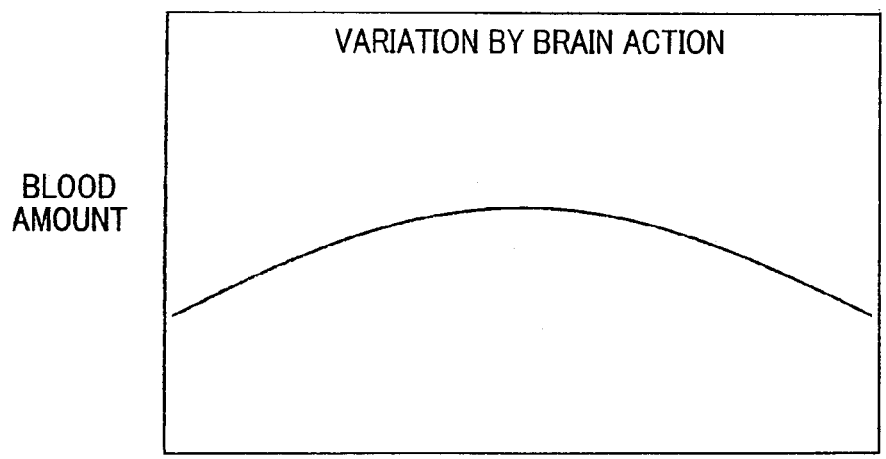
FIG. 15B is a waveform diagram of a signal indicative of blood amount variation corresponding to action of a brain.
Figure 15C:
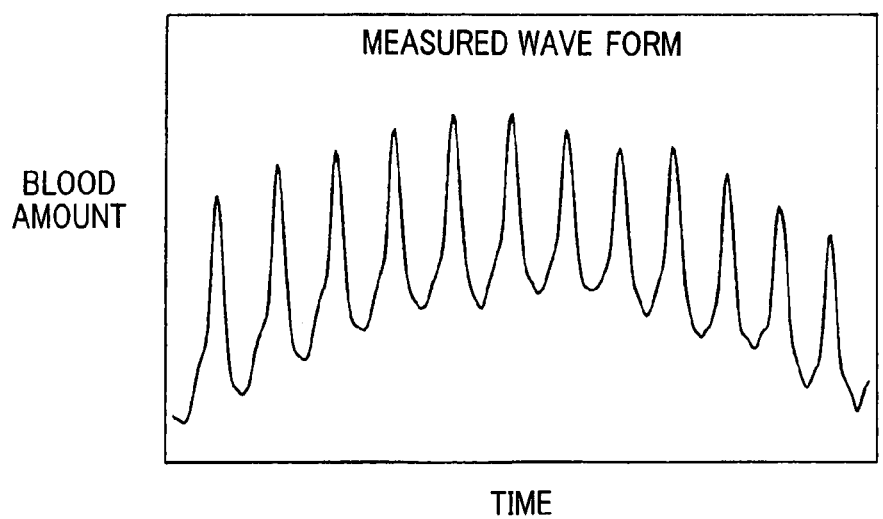
FIG. 15C is a waveform diagram of a signal indicative of blood amount variation detected on the basis of near infrared light irradiation.
Figure 18:
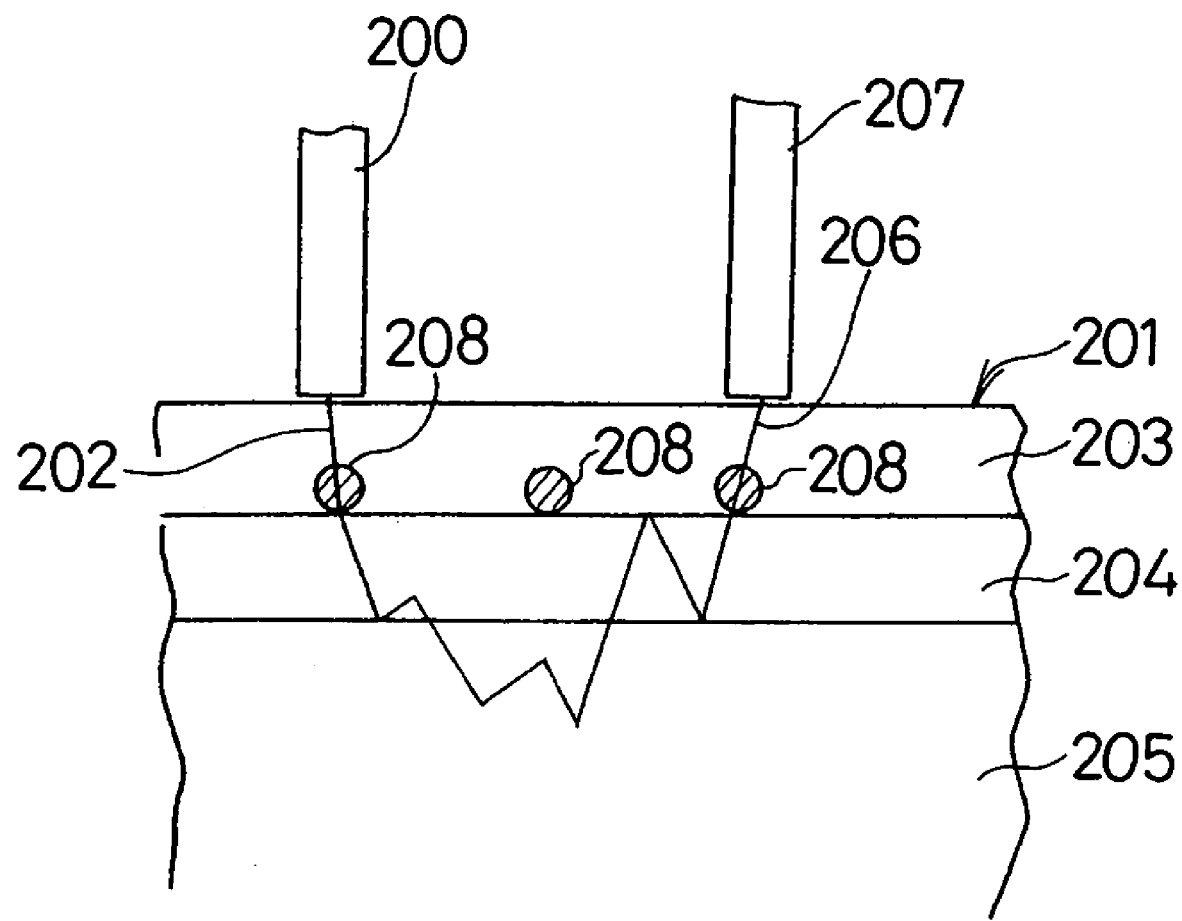
FIG. 18 is a diagram showing how the near infrared light irradiated to the head is detected as diffuse/scattering reflected light.

In the conventional optical measuring apparatus using near infrared light, there would be detected, as the intensity of scattering reflected light $I(\lambda)$, a waveform signal that overlappingly includes a pulse wave component resulting from the action of the arteries (as indicated by 208 of FIG. 18). FIGS. 15A–15C show how the waveform signal indicative of the intensity of scattering reflected light is produced. In FIGS. 15A–15C, where the horizontal axis represents time while the vertical axis represents an amount of blood. Specifically, FIG. 15A shows a signal indicative of blood amount variation based on variation over time of a pulse wave, FIG. 15B shows a signal indicative of blood amount variation produced by variation in the concentrations of oxygenated hemoglobin, deoxygenated hemoglobin and in the blood amount that result from the action of the arteries, and FIG. 15C shows a signal indicative of blood amount variation generated in detection of the intensity of scattering reflected light $I(\lambda)$. As seen from FIG. 15C, a pulse wave component is overlappingly included in the detection signal generated by the photo detector 22. Namely, the intensity of detected scattering reflected light $I(\lambda)$ can be expressed by $$I(\lambda) = Is(\lambda) + Id(\lambda) \quad \text{Mathematical Expression (2)},$$

where $Is(\lambda)$ represents the signal component corresponding to the concentrations of oxygenated hemoglobin, deoxygenated hemoglobin and blood amount and $Id(\lambda)$ represents the pulse wave component.

Because the signal representative of the intensity of the detected scattering reflected light $I(\lambda)$ overlappingly includes the pulse wave component as noted above, it has heretofore been difficult to monitor the signal corresponding to the concentrations of oxygenated hemoglobin, deoxygenated hemoglobin and blood amount that result from the action of the arteries. To give a solution to the inconvenience, the present invention is constructed to obtain a pulse wave signal from another body portion from the principal measured portion and subtract the thus-obtained pulse wave signal from the signal representative of the intensity of the detected scattering reflected light $I(\lambda)$, as illustratively shown in FIGS. 16A–16C.

Figure 16A:
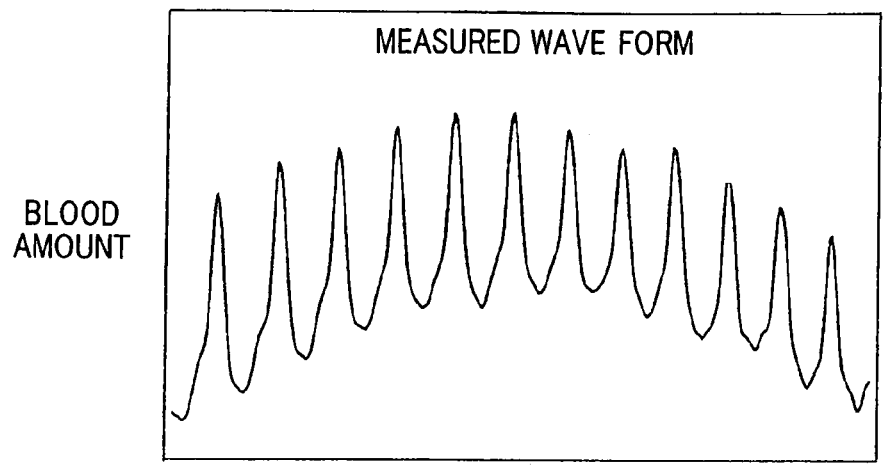
FIG. 16A is a waveform diagram of a signal indicative of blood amount variation detected on the basis of near infrared light irradiation.
Figure 16B:
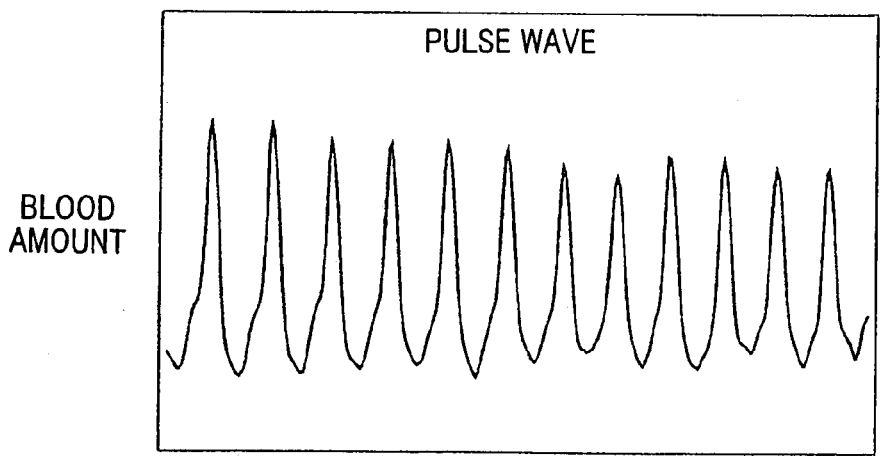
FIG. 16B is a waveform diagram of a signal indicative of blood amount variation corresponding to a pulse wave.
Figure 16C:
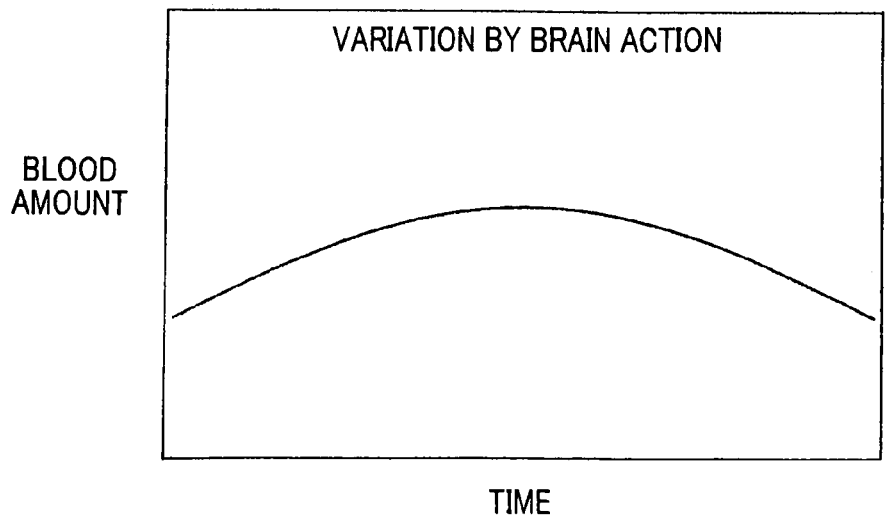
FIG. 16C is a waveform diagram of a signal indicative of blood amount variation corresponding to action of a brain.

FIG. 16A shows an output detection signal of the photo detector 22, which corresponds to "$I(\lambda)$" in Mathematical Expression (2) above. FIG. 16B shows a pulse wave signal obtained via the pulse wave sensor 103, which corresponds to "$Id(\lambda)$" in Mathematical Expression (2). Subtracting the pulse wave signal $Id(\lambda)$ from the detection signal "$I(\lambda)$" of the photo detector 22 can provide a signal to be actually monitored which corresponds to the concentrations of oxygenated hemoglobin, deoxygenated hemoglobin and blood amount that result from the action of the arteries, as illustratively shown in FIG. 16C. Such a signal to be actually monitored is obtained for each of the light of the above-mentioned three wavelengths and then simultaneous equations set on the basis of the obtained data are solved. In this way, the present invention can appropriately measure the concentrations of oxygenated hemoglobin, deoxygenated hemoglobin and blood amount resulting from the action of the arteries can be measured. The above-mentioned arithmetic operations are carried out by the arithmetic processing section 13.

In an alternative, the output detection signal "$I(\lambda)$" of the photo detector 22 may be passed through a notch filter, so as to directly remove the pulse wave signal component "$Id(\lambda)$" from the detection signal "$I(\lambda)$". There may be employed any other suitable schemes, such as one where a ratio between the amplitudes of the to-be-measured signal and pulse wave signal is determined an advance and where a given value, calculated on the basis of the previously-determined ratio and amplitude of the pulse wave signal actually measured while the brain is in action, is subtracted from an actually-measured amplitude of the detection signal of the photo detector 22.

Further, the pulse wave signal may be measured for another body portion located substantially the same distance from the heart as the principal measured portion. In this instance, the pulse wave signal measured for the other body portion presents practically the same intensity variation as the pulse wave component overlappingly included in the scattering reflected light. Note that FIGS. 15A–15C and FIGS. 16A–16C show examples of the various signals in the case where the object to be measured is a blood amount.

On the basis of the above-described principles, the second embodiment of the optical measuring apparatus 10 can provide information about the concentrations of oxygenated hemoglobin, deoxygenated hemoglobin and blood amount resulting from the action of the arteries.

Figure 17:
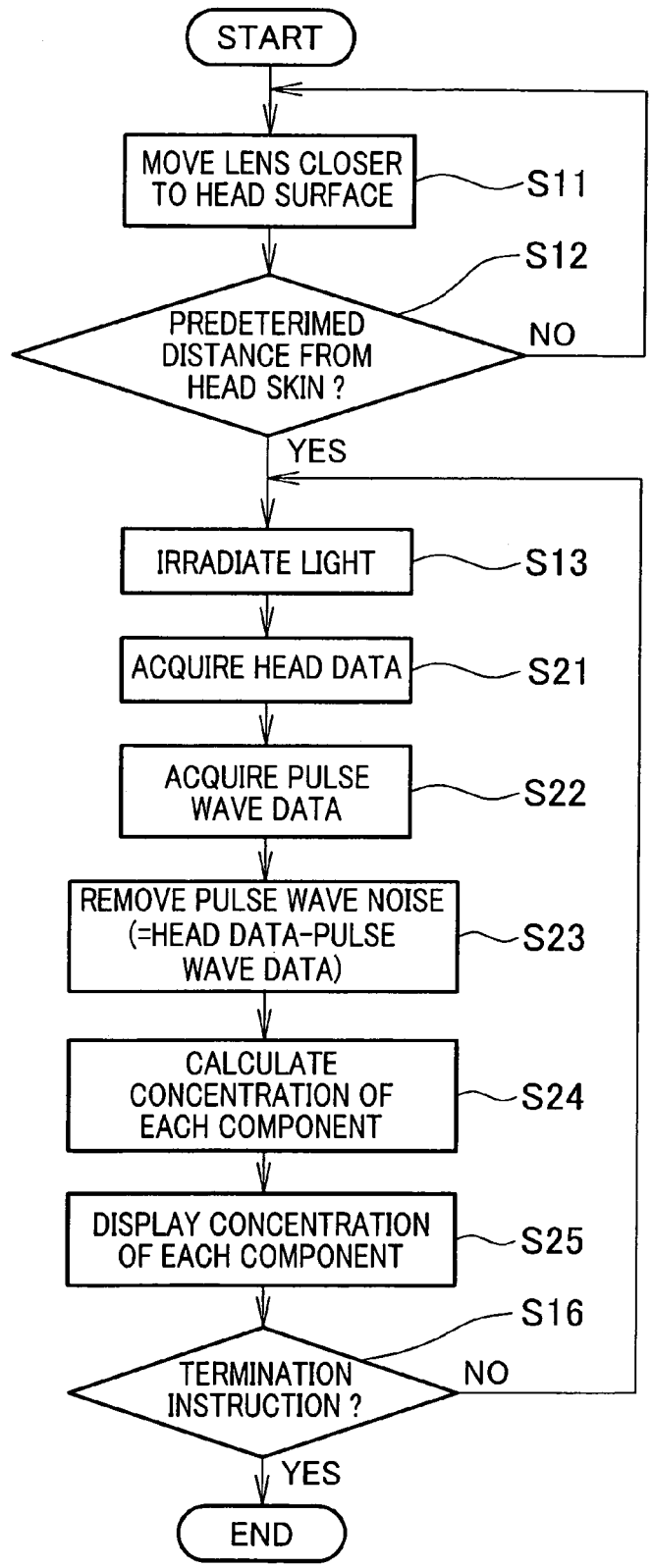
FIG. 17 is a flow chart showing a sequence of data processing performed in the second embodiment of the present invention.

Next, behavior of the second embodiment of the optical measuring apparatus 10 will be described, with reference to FIGS. 13 and 17, in relation to the case where concentrations of oxygenated hemoglobin, deoxygenated hemoglobin and all the hemoglobin in the brain are to be measured, although the biological substance to be measured may be other than hemoglobin, such as glucose, and a concentration of glucose may be measured. FIG. 17 is a flow chart explanatory of control performed in accordance with a program stored in the memory 13b of the arithmetic processing section 13.

After placing the helmet 20 on the head 1A of the to-be-measured person 1 (living body), the human operator enters a measurement start instruction via the optical measurement control section 30 to thereby start the measuring operations of the optical measuring apparatus 10. In response to the measurement start instruction, the optical measurement control section 30 executes the control program. In the flow chart of FIG. 17, steps directed to the same operations as the steps in the flow chart of FIG. 10 are assigned the same step numbers.

Then, at step S11 of FIG. 17, the light-irradiation-mechanism control device 16 is activated so that the condenser lens 49 is moved closer to the head skin by means of the feed screw mechanism 48 and motor 46. At that time, an output signal from the distance measuring device 51 near the condenser lens 49 is sent to the optical measurement control section 30, in accordance with which the control section 30 determines at step S12 whether the condenser lens 49 has reached a predetermined distance from the head skin. If answered in the affirmative (YES) at step S12, the optical measurement control section 30 sends a signal to the motor 46 to deactivate the motor 46 and terminate the movement, toward the head skin, of the condenser lens 49.

At next step S13, a light irradiation signal is sent from the optical measurement control section 30 to the light-irradiation-mechanism control device 16, so as to start near infrared light irradiation to the head of the to-be-measured person 1. At that time, the condenser lens 49 is moved or varied in angular position at high speed to scan a predetermined range, and the light source 17 is controlled, by the light-irradiation-mechanism control device 16, to alternately irradiate light of three wavelengths $\lambda_1$, $\lambda_2$ and $\lambda_3$. Then, intensity values $I(\lambda_1)$, $I(\lambda_2)$ and $I(\lambda_3)$ of scattering reflected light detected for the individual wavelengths are sent to the arithmetic processing section 13, at step S21. Concurrently, the optical measurement control section 30 measures a pulse wave signal of the same to-be-measured person 1 by means of the pulse wave detection section 101 and pulse wave sensor 103, and it sends the measured pulse wave signal value to the arithmetic processing section 22 (step S22).

In the arithmetic processing section 13, the pulse wave signal value obtained at step S22 is subtracted from the intensity value of scattering reflected light detected for each of the individual wavelengths obtained at step S21, so as to remove the pulse wave noise (step S23). Then, the arithmetic processing section 13 obtains signals $Is(\lambda_1)$, $Is(\lambda_2)$ and $Is(\lambda_3)$ corresponding to the wavelengths, and solves simultaneous equations based on Mathematical Expression (1) above. In this way, concentrations of oxygenated hemoglobin, deoxygenated hemoglobin and all the hemoglobin are calculated, and then an arithmetic operation is carried out for estimating an amount of blood from the concentration of all the hemoglobin (step S24). For the blood amount estimation, a normal hematocrit of the to-be-measured person 1 may be prestored in memory so that the amount of blood can be calculated on the basis of the prestored hematocrit. At next step S25, the measurement results are displayed on the display section 14 as numerical value data, graphs or three-dimensional distribution maps. The optical measuring apparatus 10 terminates the measurement, for example, in response to a termination instruction given from the human operator, at step S16. If no termination instruction has been given as determined at step S16, control reverts to step S13 in order to repeat the operations of steps S21–S25.

With the above-described measuring operations, the second embodiment of the optical measuring apparatus 10 can appropriately measure concentrations of oxygenated hemoglobin, deoxygenated hemoglobin and all the hemoglobin and amount of blood.

In the second embodiment of the optical measuring apparatus 10, concentration distribution of the oxygenated hemoglobin, deoxygenated hemoglobin and all the hemoglobin and distribution of blood can be obtained by providing a plurality of the optical fibers of the light irradiation mechanism 11 at different positions and detecting the intensity of the near infrared light at the different positions.

Whereas the second embodiment has been described above in relation to the case where the helmet 20 is attached to the head, there may be used a probe capable of being fit to another body portion than the head so as to measure, for the other body portion, concentrations of oxygenated hemoglobin, deoxygenated hemoglobin and all the hemoglobin and amount of blood. Further, while the second embodiment has been described above in relation to measurement of blood distribution in the brain, it can also measure distribution of glucose in blood etc. in a similar manner to the above-described.

For example, measurement values of various components in blood may be acquired by previously determining respective values, corresponding to "k" in Mathematical Expression (1), for the individual components including glucose, irradiating near infrared light of different wavelengths corresponding to the components, then determining intensity values of scattering reflected light detected for the individual wavelengths, and then solving simultaneous equations. In this way, the concentration of glucose too can be measured.

Furthermore, whereas the first and second embodiments of the optical measuring apparatus 10 have been described above in relation to measurement of the head 1A of a to-be-measured person 1, they can readily measure any other desired body portion of the to-be-measured person 1 just as in the case where the helmet 20 is used, by preparing a cover member corresponding to the other desired body portion. In addition, the light to be received by the light reception section may be scattering light transmitted through the measured body portion rather than the above-mentioned scattering reflected light.

Obviously, various minor changes and modifications of the present invention are possible in the light of the above teaching. It is therefore to be understood that within the scope of the appended claims the invention may be practiced otherwise than as specifically described.

What is claimed is:

1. An optical measuring apparatus for irradiating near infrared light to a desired portion of an object to be measured, receiving arriving light from the desired portion and acquiring information about a predetermined substance present in the desired portion on the basis of analysis of data related to the received arriving light, said optical measuring apparatus comprises:

a cover member removably attachable to the object to be measured; and a measuring unit provided on said cover member and including:

at least one light irradiation section for directly irradiating the near infrared light to the surface of the desired portion of the object; and at least one light reception section for receiving the arriving light from the desired portion of the object, wherein, in a state where said cover member is attached to the object to be measured, said light irradiation section and said light reception section are positioned out of contact with the surface of the desired portion of the object, wherein said light irradiation section includes at least one optical fiber for passing therethrough the near infrared light, the optical fiber being mounted to a movable suport that undergoes predetermined displacement during the irradiation of the near infrared light from the light irradiation section.

2. The optical measuring apparatus as claimed in claim 1 wherein the object to be measured is a human body, and said cover member is a helmet for covering a head of the human body, and wherein said light irradiation section and said light reception section have their respective distal ends positioned on an inner side of the helmet.

3. The optical measuring apparatus as claimed in claim 1 wherein said movable support comprises a scanning mechanism, and a condenser lens supported at the distal end of said light irradiation section via said scanning mechanism, and wherein, during optical measurement by said optical scanning apparatus, said condenser lens is variable, by said scanning mechanism, in an angular position thereof relative to the surface of the desired portion of the object so as to change an irradiation direction of the near infrared light.

4. The optical measuring apparatus as claimed in claim 3 wherein said scanning mechanism includes a piezoelectric element, and variation in the angular position of said condenser lens is effected by control of a voltage to be applied to said piezoelectric element.

5. The optical measuring apparatus as claimed in claim 1 wherein said movable support comprises a scanning mechanism, and wherein a whole of said light irradiation section is supported by said scanning mechanism, and wherein, during optical measurement by said optical scanning apparatus, said light irradiation section is variable, by said scanning mechanism, in an angular position thereof relative to the surface of the desired portion of the object so as to change an irradiation direction of the near infrared light.

6. The optical measuring apparatus as claimed in claim 1, wherein said movable support comprises an adjustment section mounted on an outside of the cover member for supporting said light irradiation section; and wherein the adjustment section includes a ring motor for moving said light irradiation section in an axial direction thereof with respect to the surface of the desired portion of the object to thereby adjust a distance between said light irradiation section and the surface of the desired portion of the object to be measured.

7. The optical measuring apparatus as claimed in claim 1 wherein the arriving light is diffuse/scattering reflected light from the desired portion of the object to be measured.

8. The optical measuring apparatus as claimed in claim 1 wherein the object to be measured is a human body, and the predetermined substance is blood, and wherein said optical measuring apparatus optically measures an amount of blood in the desired portion of the object.

9. The optical measuring apparatus as claimed in claim 1, further comprising:

a light detection mechanism for detecting the arriving light received by said at least one light reception section, the object being a living body;

a pulse wave detection section for detecting a pulse wave in another portion of the living body separate from the desired portion and thereby generating a signal indicative of the detected pulse wave;

an arithmetic operation section for subtracting pulse wave data, obtained on the basis of the signal generated by said pulse wave detection section, from measurement data obtained on the basis of the arriving light detected by said light detection mechanism; and a display section for displaying a result of an arithmetic operation performed by said arithmetic operation section.

10. The optical measuring apparatus as claimed in claim 9 wherein said at least one light irradiation section includes at least one light source for emitting light of a wavelength in a near infrared range, and at least one optical fiber for transmitting therethrough the light emitted by said light source.

11. The optical measuring apparatus as claimed in claim 10 wherein said moveable support includes:

a condenser lens provided at a distal end of said optical fiber;

a feedscrew mechanism for controlling a distance between said condenser lens and a surface of the desired portion of the living body to be measured; and a piezoelectric element contractible or expandable in response to a voltage applied thereto so as to control an angular position of said condenser lens relative to the surface of the desired portion.

12. The optical measuring apparatus as claimed in claim 9 wherein said at least one light irradiation section includes a light source for emitting light of a wavelength in a near infrared range, a spectroscope for dispersing the light emitted by said light source, and an optical fiber for outputting the light dispersed by said spectroscope.

13. The optical measuring apparatus as claimed in claim 9 wherein said light detection mechanism includes photo detector means sensitive to a plurality of different near infrared wavelength regions.

14. The optical measuring apparatus as claimed in claim 9 wherein the other portion of the living body is located substantially the same distance from a heart of the living body as the desired portion.

15. The optical measuring apparatus as claimed in claim 9 wherein the other portion of the living body is an earlobe.

16. The optical measuring apparatus as claimed in claim 9 wherein the information about the predetermined biological substance pertains to at least one of a concentration of oxygenated hemoglobin, a concentration of deoxygenated hemoglobin, a concentration of all the hemoglobin and an amount of blood in the desired portion.

17. The optical measuring apparatus as claimed in claim 9 wherein the information about the predetermined biological substance pertains to a concentration of glucose in the desired portion.

18. The optical measuring apparatus as claimed in claim 9 wherein the desired portion of the living body is a head of a human body.

19. The optical measuring apparatus as claimed in claim 9 wherein the arriving light from the desired portion of the living body is diffuse/scattering reflected light produced by the irradiated near infrared light entering the desired portion of the living portion, then repeating reflection, refractive transmission and scattering in the desired portion and then getting out of the desired portion toward said light detection section.

20. The optical measuring apparatus as claimed in claim 1, further comprising a controlling computer including a program to perform an optical measuring process, said program comprising:
  a step of moving, by means of said movable support, said at least one optical fiber so that a light outputting end of said at least one optical fiber gets closer to the desired portion of an object to be measured;
  a step of determining, on the basis of a distance value measured by distance measuring means, whether the light outputting end of said at least one optical fiber has reached a predetermined position near a surface of the desired portion;
  a step of irradiating near infrared light, emitted by a light source, to the desired portion of the object via the light outputting end of said at least one optical fiber while, by means of a scanning mechanism, causing the light outputting end to make scanning movement relative to the surface of the desired portion;
  a step of removing a pulse wave detection signal representative of a pulse wave detected by pulse wave detection means from a light detection signal representative of scattering reflected light detected by light detection means; and
  a step of calculating, on the basis of the light detection signal having the pulse wave detection signal removed therefrom by said step of removing, a concentration of a biological substance present in the desired portion of the object to be measured.

21. An optical measuring apparatus for irradiating near infrared light to a desired portion of an object to be measured, receiving arriving light from the desired portion and acquiring information about a predetermined substance present in the desired portion on the basis of analysis of data related to the received arriving light, said optical measuring apparatus comprises:
  a cover member removably attachable to the object to be measured; and
  a measuring unit provided on said cover member and including:
  at least one light irradiation section for irradiating the near infrared light to the desired portion of the object; and
  at least one light reception section for receiving the arriving light from the desired portion of the object,
  wherein, in a state where said cover member is attached to the object to be measured, said light irradiation section and said light reception section are positioned out of contact with the desired portion of the object, and further comprising:
  a ring motor mounted on an outer side of the cover member for moving said light irradiation section an axial direction thereof with respect to a surface of the desired portion of the object to thereby adjust a distance between said light irradiation section and the surface of the desired portion of the object to be measured; and
  a plurality of piezoelectric elements mounted on an inner side of the cover member for changing an irradiation direction of the near infrared light relative to the surface of the desired portion of the object.

22. The optical measuring apparatus as claimed in claim 1, wherein an optical fiber of the light irradiation section and the light reception section are out of contact with the surface of the desired portion of the object.

* * * * *